(12) United States Patent
Humphreys

(10) Patent No.: US 6,642,356 B1
(45) Date of Patent: Nov. 4, 2003

(54) PEPTIDES WHICH FUNCTION AS HINGE REGIONS IN PROTEIN

(75) Inventor: David Paul Humphreys, Maidenhead (GB)

(73) Assignee: Celltech Therapeutics Limited, Berkshire (GB)

( * ) Notice: Subject to any disclaimer, the term of this patent is extended or adjusted under 35 U.S.C. 154(b) by 0 days.

(21) Appl. No.: 09/508,930

(22) PCT Filed: Sep. 21, 1998

(86) PCT No.: PCT/GB98/02851

§ 371 (c)(1),
(2), (4) Date: Mar. 17, 2000

(87) PCT Pub. No.: WO99/15549

PCT Pub. Date: Apr. 1, 1999

(30) Foreign Application Priority Data

Sep. 19, 1997 (GB) .............................. 9720054

(51) Int. Cl.[7] .............................. C07K 4/00; C07K 7/08; C07K 16/00
(52) U.S. Cl. .................... 530/327; 530/300; 530/350; 530/387.1; 530/387.3; 530/391.1; 530/391.3; 530/391.5; 530/391.7; 530/391.9; 530/402; 530/866; 530/867
(58) Field of Search ................. 530/300, 327, 530/350, 387.1, 387.3, 391.1, 391.3, 391.5, 391.7, 391.9, 402, 866, 867

(56) References Cited

U.S. PATENT DOCUMENTS 5,041,533 A   8/1991 Wunsch et al.
5,635,371 A  * 6/1997 Stout et al.

FOREIGN PATENT DOCUMENTS

EP       284 898       3/1988

OTHER PUBLICATIONS

Crasto et al. Protein Engineering 2000; 13(5):309–312.*
Better et al., *PNAS USA*, 90:457–61 (1993).
Humphreys et al, *J. Immunol. Methods*, 209:193–202 (1997).
Kaku et al., *General pharmacology*, 27:435 (1996).
King et al., *Biochemical J.*, 281:317 (1992).
Lyons et al., *Protein Engineering*, 3:703 (1990).
Pack et al., *Biochem.*, 31:1579 (1992).
Rodrigues et al., *J. Immunology*, 151:6954–61 (1993).

* cited by examiner

*Primary Examiner*—Phillip Gambel
*Assistant Examiner*—Jessica H. Roark
(74) *Attorney, Agent, or Firm*—Klauber & Jackson

(57) ABSTRACT

Peptides comprising the amino acid sequence set forth in SEQ ID NO:1 are described wherein the amino acid at position 7 of SEQ ID NO:1 and the amino acid at position 8 of SEQ ID NO:1, which may be the same or different, is each a neutral aliphatic L-ammo acid residue, and protected and reactive derivatives thereof. The peptides may be used as hinge regions in proteins, wherein they are capable of being covalently coupled to achieve dimeric structures, for example, as found in antibodies.

10 Claims, 5 Drawing Sheets

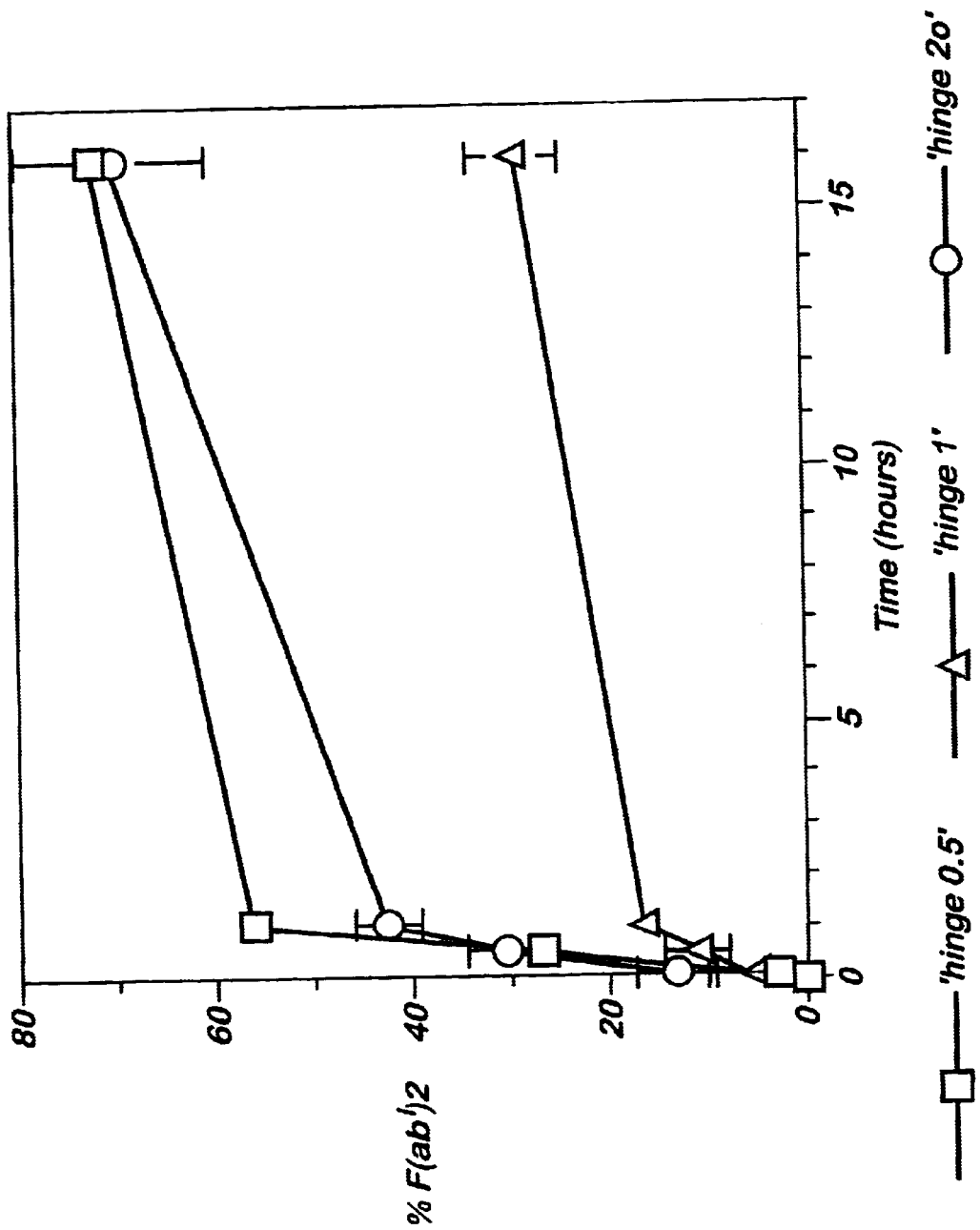

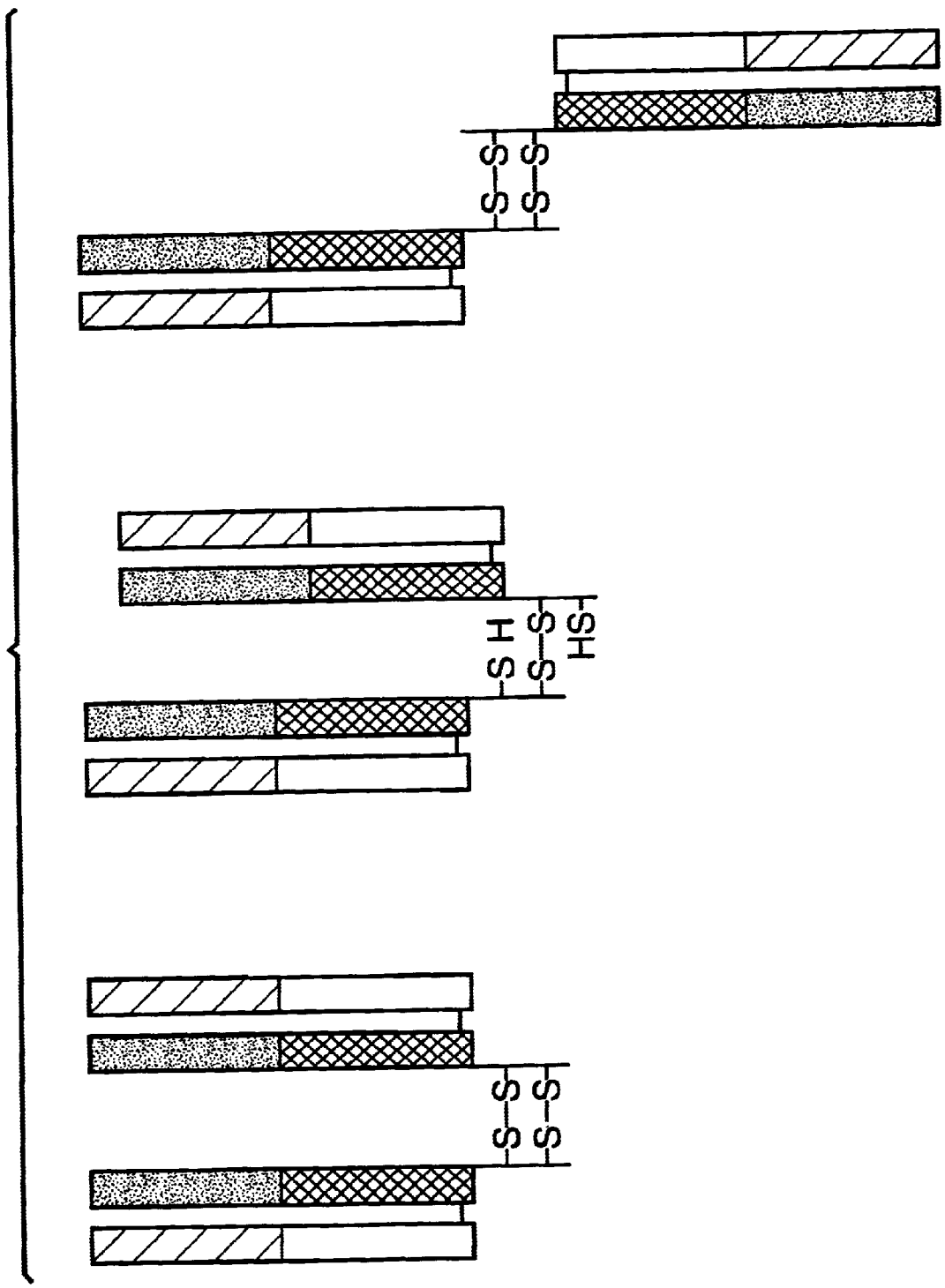

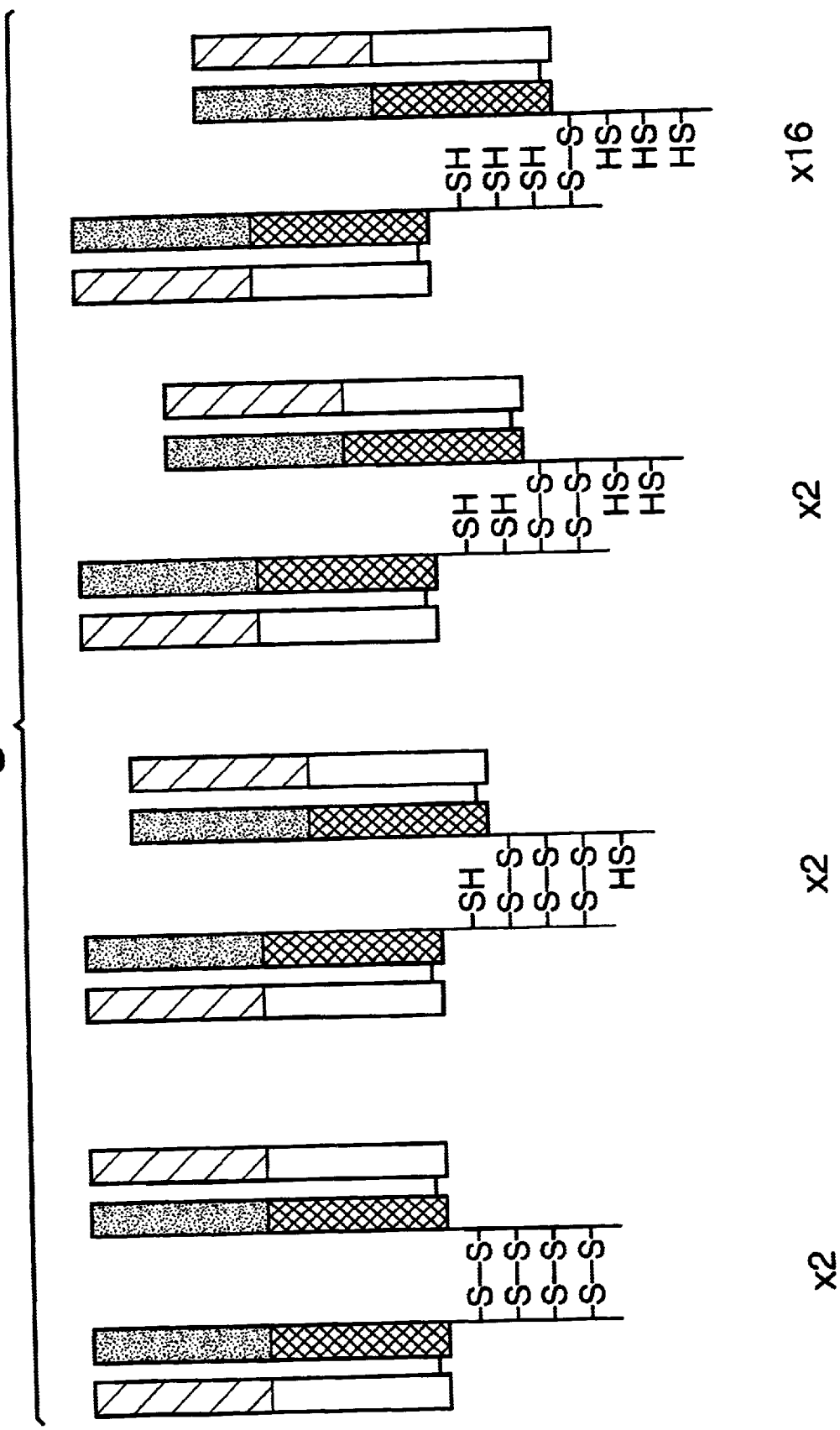

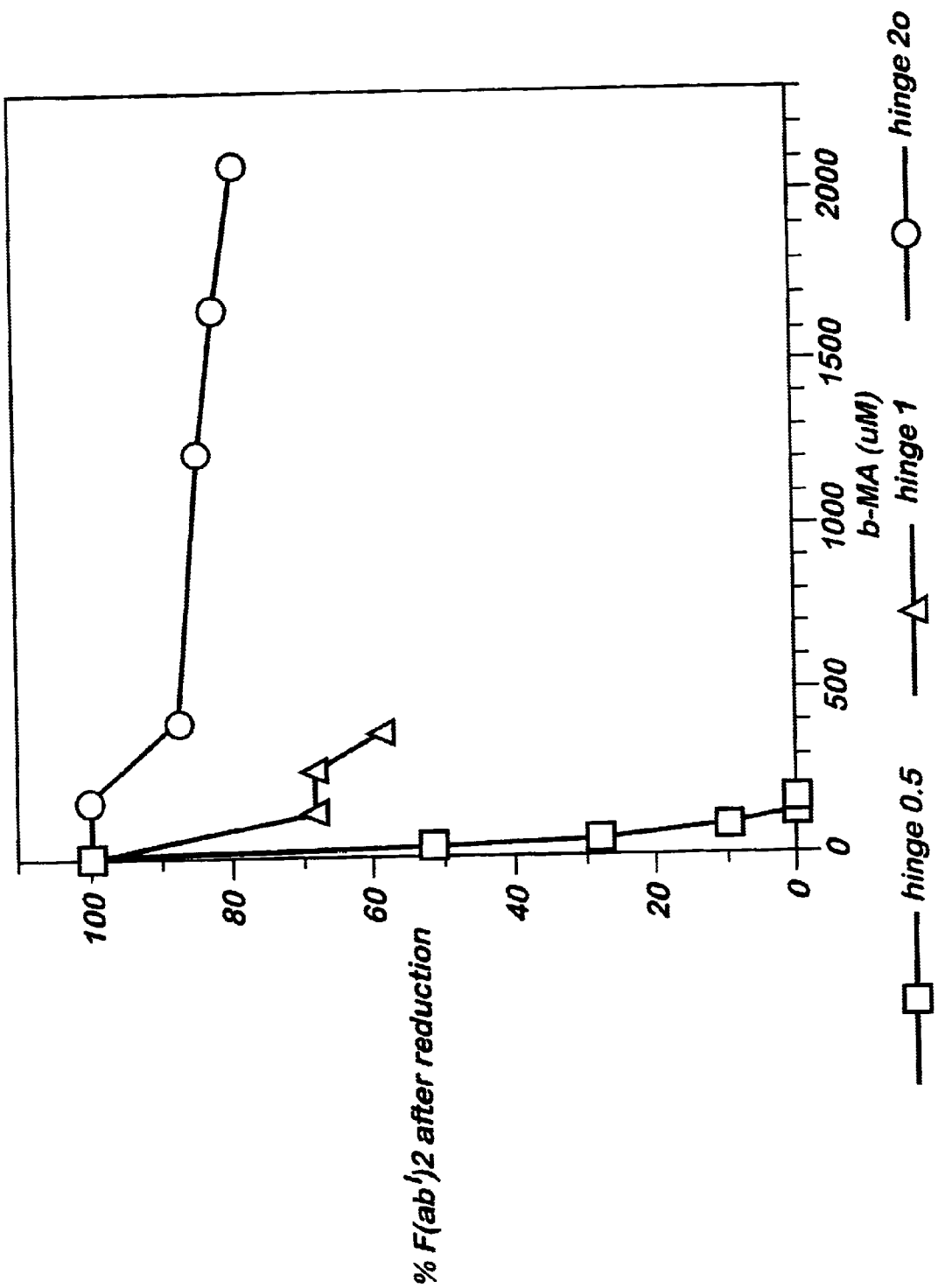

PEPTIDES WHICH FUNCTION AS HINGE REGIONS IN PROTEIN

Priority is claimed under 35 U.S.C. 371 to PCT/GB98/012851 filed Sep. 21, 1998.

This invention relates to peptides which function as hinge regions in proteins, to proteins containing such hinge regions and to the use of said proteins in medicine.

In clinical antibody therapy and imaging applications the avidity of a dimeric antibody species is often required to achieve an effective antibody affinity in vivo, but without the effector functions or lengthy serum permanence conferred by the Fc domain (ref. 1–3—for the literature referenced by number herein see the list "References" hereinafter). F(ab')2 molecules meet this requirement and can be produced by proteolytic cleavage of monoclonal IgG of appropriate isotypes, or by use of recombinant immunoglobulin derived domains produced in E. coli.

The ability to secrete antibody fragments to the oxidising periplasm of E. coli has led to rapid advances in the engineering of grafted, highly expressed Fab's. Importantly, the use of E. coli also enables the cost effective and rapid production of the amounts of antibody material required to supply a large market (ref. 4, 5). Engineered Fab' is often expressed with only one hinge-cysteine. This cysteine can be used for attachment of other Fab's to make a $F(ab')_2$ or attachment of therapeutic effector molecules such as radionuclides, enzymes, or toxins (ref. 6).

Several protein engineering approaches for producing divalent antigen binding species in vivo in E. coli have been reported, using both modified scFvs and Fab's. Simple hinge modifications do not give substantial yields in vivo of dimeric species from E. coli (ref. 7–9). Techniques for increasing dimerisation in vivo are well characterised, but these often use large non-immunoglobulin dimerisation motifs which are potentially immunogenic and can cause severe reductions in the level of expression of soluble protein (ref. 10–13). The simplest route to production of dimeric antigen binding species remains the direct disulphide or chemical cross-linking of Fab's in vitro (ref. 2, 7, 14, 15). The choice of covalent linkage between the two Fab's is an important one. If the $F(ab')_2$ is cleaved in vivo then the resulting Fab' molecules generated suffer both from loss of avidity and very rapid clearance from the circulation (ref. 1, 2). Single disulphide bonds are known to be more susceptible to cleavage in vivo than protected disulphides, sulphide, or thioether bonds (ref. 2, 9, 16). However, two disulphides as found in the hinge region of $F(ab')_2$ isolated from proteolytic cleavage of IgG1 have previously been found to be as robust as one thioether bond, as judged by serum permanence (ref. 9).

There is a need for non-immunogenic dimeric antibody species which overcome the problem of facile in vivo cleavage while still being efficient to manufacture and couple to other effector molecules. We have now found a peptide, which when part of a larger protein such as a Fab' fragment efficiently generates dimers and yields dimeric material which is highly resistant to chemical reduction in vitro and has long serum permanence times in vivo. Advantageously, the peptide is well tolerated in E. coli and in our tests to date has been shown to be non-immunogenic.

Thus according to one aspect of the invention we provide a peptide of formula (1) (SEQ ID NO:1):

$^N$TCPPCPXYCPPCPA$^C$     (1)

wherein X and Y, which may be the same or different, is each a neutral aliphatic L-amino acid residue, and protected and reactive derivatives thereof.

In formula (1) and the other peptides described herein conventional single letter abbreviations are used to represent amino acid residues except where otherwise indicated. The superscripts "N" or "C" are used to indicate respectively the N- or C-terminal residue of a peptide.

Neutral L-amino acid residues represented by each of the groups X and Y include glycine, alanine, valine, leucine, isoleucine, serine and threonine residues.

Protected derivatives of the peptides of formula (1) include N- and C-terminal protected derivatives in which the N-terminal amino group or the C-terminal carboxyl group is linked to a protecting group. N-protected derivatives include for example optionally substituted benzyloxycarbonylamino, allyloxycarbonylamino, cycloalkyloxycarbonylamino, t-butoxycarbonylamino, trifluoroacetylamino, phthalylamino, aralkylamino, e.g. benzylamino, diphenylmethylamino or triphenylmethylamino, tosyl-amino or formylamino derivatives. C-protected derivatives include for example esters, such as optionally substituted alkyl, e.g. methyl, ethyl or t-butyl, aralkyl, e.g. benzyl or benzhydryl, silyl, e.g. trimethylsilyl and phthalimidomethyl esters, and esters with polymers, for example functionalised styrene-based resins.

Reactive derivatives of peptides of formula (1) include those in which the C-terminal carboxyl group is functionalised, and is, for example, an acyl halide such as an acyl chloride, an aryl cyanide or azide, an anhydride, an ester, for example a N-hydroxy succinimide, p-nitrophenyl or pentachloro-phenyl ester, a N-acyl heterocycle such as a N-acyl imidazole, pyrazole or triazole or an activated acid formed by addition of a carbodiimide or isoxazolium reagent.

Particularly useful peptides of formula (1) include those wherein X is an alanine residue, In another preference, Y in particular is a threonine residue. An especially useful peptide according to the invention has the formula (2) (SEQ ID NO:2):

$^N$TCPPCPATCPPCPA$^C$     (2)

and protected and reactive derivatives thereof.

BRIEF DESCRIPTION OF THE DRAWINGS

FIG. 1. Effect of hinge sequences and duration of oxidation on $F(ab')_2$ formation in vitro.

Figure 4:
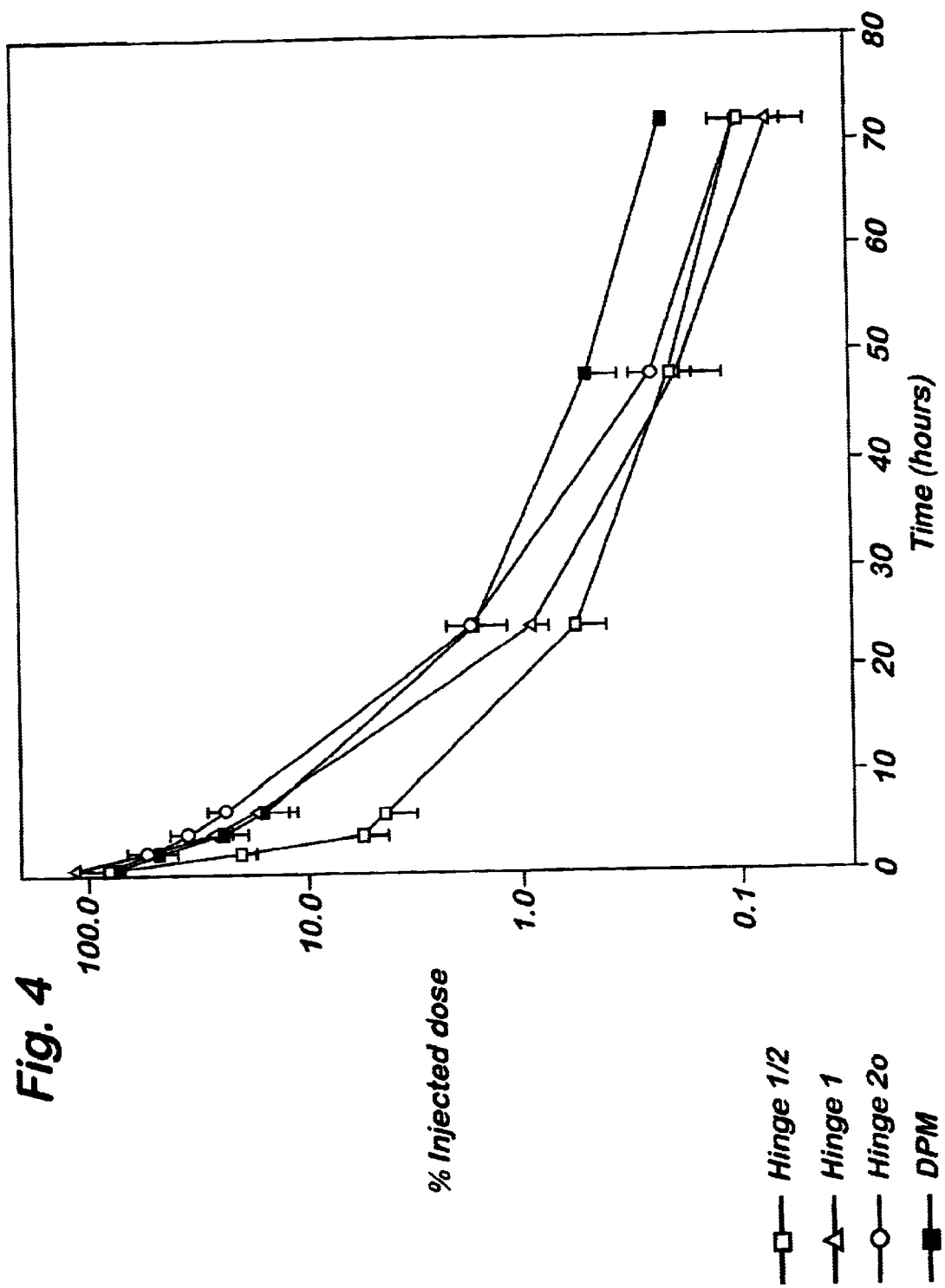

The mean and SD of three independent experiments conduction at pH 8.0 and room temperature are shown.

FIG. 2. Range of F(Ab')$_2$ molecules capable of being formed

A. $F(ab')_2$ formed by 'hinge 1', and B, $F(ab')_2$ formed by 'hinge 2o', only the 'head to head' forms are shown for 'hinge 2o', hence the use of 'x2' to denote possible 'head to tail' forms.

FIG. 3. Effect of hinge sequence on resistance of $F(ab')_2$ to reduction in vitro F(Ab')$_2$ at 0.25 mgml$^{-1}$ are subjected to reduction at pH 7.0, 37° C. for 45 min. at the range of β-ME concentrations shown.

FIG. 4. Effect of hinge composition on $F(ab')_2$ pharmacokinetics in rat.

The mean and standard error of mean for each $F(ab')_2$ are shown. There were six animals in each group, except 'hinge 2o' where n=10.

DETAILED DESCRIPTION OF THE INVENTION

The peptides according to the invention may be prepared from appropriately activated and/or protected amino acids

[for example utilising reactive derivatives and protecting groups of the types mentioned in connection with the peptides of formula (1)] using routine peptide synthesis techniques [see for example Merrifield, B. Science (1985), 232, 341–347].

The presence of four cysteine residues in each peptide of formula (1) provides four centers for disulphide and/or thioether bond formation thus allowing reaction with other molecules containing thiol reactive groups. In particular dimeric proteins may be obtained by incorporating the peptides in protein chains and the invention extends to such a use. In order to achieve protein dimerization a peptide of formula (1) must first be coupled to an exiting protein chain or synthesized de novo as part of it and we therefore provide in another aspect of the invention a protein comprising one polypeptide chain characterized in that said chain contains an amino acid sequence (SEQ ID NO:1) $^N$TCPPCPXYCP-PCPA$^C$. wherein X and Y are as defined for the peptide of formula (1).

The invention also extends to proteins containing two polypeptide chains covalently linked via the cysteine residues in $^N$TCPPCPXYCPPCPA$^C$ (SEQ ID NO:1) as explained above and thus according to a further aspect of the invention we provide a protein comprising two polypeptide chains characterized in that each of said chains contains an amino acid sequence $^N$TCPPCPXYCPPCPA$^C$ (SEQ ID NO:1) wherein X and Y are as defined for the peptide of formula (1) and each chain is covalently linked to the other through one, two, three or four of the cysteine residues present in each of said amino acid sequences.

In the proteins according to the invention the amino acid sequence $^N$TCPPCPXYCPPCPA$^C$ (SEQ ID NO:1) is preferably a sequence $^N$TCPPCPXYCPPCPA$^C$ (SEQ ID NO:3) or $^N$TCPPCPXYCPPCPA$^C$ (SEQ ID NO:4), especially the sequence $^N$TCPPCPATCPPCPA$^C$ (SEQ ID NO:2)

The proteins according to the invention may be naturally occurring proteins to which the peptide of formula (1) has been coupled, or recombinant proteins incorporating the amino acid sequence $^N$TCPPCPXYCPPCPA$^C$ (SEQ ID NO:1). The proteins may generally be structural or, especially, binding proteins. Particular binding proteins include hormones, cytokines, colony stimulating factors, growth factors, releasing factors, ion carriers, toxins, and receptors thereof, including all or part of receptors associated with binding to cell surface associated molecules, the T-cell receptor, CD4, CD8, CD28, cytokine receptors, e.g. an interleukin receptor, TNF receptor or interferon receptor, receptors for colony stimulating factors e.g. G-CSF or GM-CSF, platelet derived growth factors e.g. PDGF-α and PDGF-β, and in particular antibodies and antigen binding fragments thereof.

Where the protein according to the invention has one peptide chain containing a $^N$TCPPCPXYCPPCPA$^C$ (SEQ ID NO:1) amino acid sequence it may be a monomeric protein or be separately linked to one ore more other polypeptide chains to form overall a multimeric structure. In those proteins of the invention containing two polypeptide chains with covalently linked $^N$TCPPCPXYCPPCPA$^C$ (SEQ ID NO:1) sequences the protein will clearly be at least diemric but may also consist of other, separately linked chains to form overall a multimeric structure. Dimers and multimers may be composed of more than one type of polypeptide chain and be homo- or heteromeric.

The production, of proteins according to the invention may be achieved using standard chemical or recombinant DNA techniques. Chemical techniques include chemical coupling of a protein and a peptide of formula (1) using activated and protected derivatives of the protein and peptide as described above in relation to the production of peptides of formula (1). In this way, for example, a peptide of formula (1) may be site-specifically coupled to the C-terminal end of a suitably C-activated protein.

Recombinant DNA techniques generally involve the expression of a protein by a host cell, followed by recovery of the protein using standard separation and purification techniques. DNA coding for the protein may be introduced into any suitable expression vector by operatively linking the DNA to any necessary expression control elements therein and transforming any suitable procaryotic or eucaryotic host cell with the vector using well known procedures: A more detailed description of suitable techniques is given hereinafter in relation to the production of antibodies according to the invention. These may be generally followed and/or easily adapted to enable the production of any protein according to the invention by recombinant means. The use of recombinant DNA technology provides a flexible approach to proteins according to the invention in that it enables the easy manipulation and insertion of a peptide of formula (1) at any desired position in a protein. DNA coding for a peptide of formula (1) is thus particularly useful and forms a further aspect of the invention DNA containing the following nucleotide sequence:

5' ACATGCCCGCCGTGCCCGGCGACCTGC-CCGCCGTGCCCGGCG 3' (SEQ ID NO:5) where each letter is the standard code for a nucleotide coding for the amino acid sequence $^N$TCPPCPATCPPCPA$^C$ (SEQ ID NO:2) is especially useful and the invention extends to DNA comprising this sequence together with variants thereof wherein one ore more nucleotides have been substituted due to the degeneracy of the genetic code. The invention also extends to recombinant plasmids containing DNA coding for a peptide of formula (1), to cells containing said plasmids and to a process for producing a protein according to the invention which comprises culturing said cells such that the desired protein is expressed and recovering the protein from the culture.

The amino acid sequences $^N$TCPPCPXYCPPCPA$^C$ (SEQ ID NO:1) are particularly suitable for use with binding proteins such as cell-associated receptors or antibodies where each sequence can function as a hinge region to provide a dimerisation capacity. Thus, for example, recombinant receptors (see for example International Patent Specifications Nos. WO 92/100591, WO 92/15322, WO 93/19163, WO 95/02686 and WO 97/23613) can be designed which incorporate these sequences to facilitate dimerisation of the individual receptor chains required for efficient receptor binding and the invention extends to a recombinant receptor comprising at least one peptide of formula (1). Such receptors are of use for example to redirect and activate cells [see the patent specifications just mentioned] and the invention includes such cells expressing a recombinant receptor comprising at least one peptide of formula (1).

In antibodies the sequences $^N$TCPPCPXYCPPCPA$^C$ (SEQ ID NO:1) can be used as substitutes for naturally occurring hinge regions (the hinge region is located between the $C_H1$ and $C_H2$ domains in naturally occurring immunoglobulins). The sequences are particularly suited for this purpose and in a preferred aspect of the invention we provide an antibody containing a hinge region characterised in that said hinge region has an amino acid sequence $^N$TCPPCPXYCPPCPA$^C$ (SEQ ID NO:1) where X and Y are as defined for formula (1). In this instance, the hinge region preferably has an amino acid sequence $^N$TCPPCPXYCPPC-PA$^C$ (SEQ ID NO:1) or $^N$TCPPCPXTCPPCPA$^C$ (SEQ ID NO:4), more especially $^N$TCPPCATCPPCPA$^C$ (SEQ ID NO:2).

The term "antibody" as used herein is generally intended to include monovalent, divalent or other multivalent antibodies. Thus for example a monovalent antibody according to the invention may be a single chain comprising an immunoglobulin heavy chain variable ($V_H$) domain and a $^N$TCPPCPXYCPPCPA$^C$ (SEQ ID NO:1) hinge region directly attached to it, preferably at the C-terminal end of the $V_H$ domain. Alternatively, the $V_H$ domain and hinge region may be separated by a spacer region comprising one or more amino acids in peptide linkage to each other and the rest of the antibody. The spacer region may be for example one or more immunoglobulin heavy ($C_H$) or light ($C_L$) chain constant domains or fragments thereof for example a CHI domain or a fragment thereof and/or a $C_N2$ and/or a $C_N3$ domain or fragments thereof. Where desired the hinge region may have one or more other amino acids attached to its C-terminus for example one or more immunoglobulin constant region domains or fragments thereof as just described. The $V_H$ domain may be monomeric or it may be dimeric and contain $V_H$-$V_H$ or $V_H$-$V_L$ (where $V_L$ is an immunoglobulin light chain variable domain) dimers in which the $V_H$ and $V_L$ chains are non-covalently associated. Where desired however, the chains may be covalently coupled either directly, for example via a disulphide bond between the two variable domains, or through a linker, for example a peptide linker, to form a single chain domain. Particular examples of monovalent antibodies according to the invention include Fv, single chain Fv and especially Fab or Fab' fragments each containing a hinge region having the sequence $^N$TCPPCPXYCPPCPA$^C$ (SEQ ID NO:1).

Divalent antibodies according to the invention include two of the monomeric chains just described covalently linked through one, two, three or four of the cysteine residues of the hinge region $^N$TCPPCXYCPPCPA$^C$ (SEQ ID NO:1) of each chain. The linkage may be a simple disulphide linkage or may be via a linker group, for example as described in International Patent Specifications Nos. WO 90/09195 and WO 90/09196. Particular divalent antibodies include F(ab)$_2$ and F(ab')$_2$ fragments.

Multivalent antibodies according to the invention include for example tri- and tetravalent antibodies comprising three or four of the monomeric chains described above linked via their hinge regions by a linker, for example as described in International Patent Specification No. 92/22583.

The antibody according to the invention will in general be capable of selectively binding to an antigen. The antigen may be any cell-associated antigen, for example a cell surface antigen such as a T-cell, endothelial cell or tumour cell marker, or it may be a soluble antigen. Particular examples of cell surface antigens include adhesion molecules, such as E-selectin, P-selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4 IL-5, IL-6 IL-8 or IL-12, viral antigens, for example respiratory syncytial virus or cytomegalovirus antigens, interferons such as interfaron-α, Interferon-β or interferon-y, tumour necrosis factor-α, tumour necrosis factor-β, colony stimulating factors such as G-CSF or GM-CSF, and platelet derived growth factors such as PDGF-α, and PDGF-β and where appropriate receptors thereof.

The variable region domain(s) may be any naturally occurring variable domain or an engineered version thereof. By engineered version is meant a variable region domain which has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one complementarity determining region (CDR) and optionally one or more framework amino acids from one antibody and the remainder of the variable region domain from a second antibody.

Antibodies according to the invention may be obtained from any whole antibody, especially a whole monoclonal antibody, [prepared by conventional immunisation and cell fusion procedures], using any suitable standard enzymatic cleavage and/or digestion techniques, for example by treatment with pepsin followed by chemical coupling with a peptide of formula (1) or a protected or activated derivative thereof using routine protein synthesis techniques as described above in relation to the production of peptides of formula (1). Alternatively, the antibody of the invention may be prepared by the use of recombinant DNA techniques involving the manipulation and re-expression of DNA encoding antibody variable and/or constant regions. Such DNA is known and/or is readily available from DNA libraries including for example phage-antibody libraries [see Chiswell, D. J. and McCafferty, J. Tibtech. 10 80–84 (1992)] or where desired can be synthesised. Standard molecular biology and/or chemistry procedures may be used to sequence and manipulate the DNA, for example, to introduce codons to create a sequence $^N$TCPPCPXYCPPCPA$^C$, to modify, add or delete other amino acids or domains as desired.

From here, one or more replicable expression vectors containing the DNA may be prepared and used to transform an appropriate cell line, e.g. a non-producing myeloma cell line, such as a mouse NSO line or a bacterial, e.g. *E. coli* line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International pic sequencing handbook; and site directed mutagenesis ban be carried out according to the method of Kramer et al [Nucl. Acids Res. 12. 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967. Once expressed, the antibody may be separated from the host cell and purified using standard centrifugation, filtration, chromatography and other separation/purification techniques, for example as described in the Examples hereinafter.

Antibody fragments containing a sequence $^N$TCPPCPXY-CPPCPA$^C$ (SEQ ID NO:1), particularly Fab or Fab' fragments are particularly suited for manufacture in *E. coli* as described above and in the Examples herein.

Where desired, the protein, including antibody, according to the invention may have one or more effector or reporter molecules attached to it and the invention extends to such modified proteins and, in particular, antibodies. The effector or reporter molecules may be attached to the protein through any available amino acid side-chain or terminal amino acid functional group located in the protein, for example any free amino, imino, hydroxyl or carboxyl group. In one preference however the molecule may be attached to a cysteine residue in an amino acid sequence $^N$TCPPCPXYCPPCPA$^C$ (SEQ ID NO:1). Dimers containing these sequences are particularly resistant to chemical reduction in vitro and advantageously can be partially reduced to expose reactive thiols to which effector or reporter molecules may be attached. One, two, three or more effector or reporter molecules may be attached in this way.

Effector molecules include, for example, antineoplastic agents, toxins (such as enzymatically active toxins of bacterial or plant origin and fragments thereof e.g. ricin and fragments thereof) biologically active proteins, for example enzymes, synthetic or naturally occurring polymers, nucleic acids and fragments thereof, e.g. DNA, RNA and fragments thereof, radionuclides, particularly radioiodide, and chelated metals. Suitable reporter groups include chelated metals, fluorescent compounds or compounds which may be detected by NMR or ESR spectroscopy.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, tfiethylenethiophosphor-amide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperamicin and derivatives thereof, mitotic inhibitors, such as etoposide, vincristine or vinblastine and derivatives thereof, alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e g. tamoxifen); anthraquinones, such as mitoxantrone, ureas, such as hydroxyurea; hydrazines, such as procarbazine; or imidazoles, such as dacarbazine.

Synthetic or naturally occurring polymers include for example optionally substituted straight or branched chain polyalkylene, polyalkenylene or polyoxyalkylene polymers such as polyethyleneglycol, polypropylene glycol, polyvinylalcohol and especially, methoxypolyethylene glycol or branched or unbranched polysaccharides, e.g. a homo- or hetero-polysaccharide such as lactose, amylose, dextran or gylcogen.

Chelated metals include chelates of di-or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Co, $^{195}$Au, $^{199}$Au, $^{110}$Ag, $^{203}$Pb, $^{206}$Bi, $^{207}$Bi, $^{111}$In, $^{67}$Ga, 68Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

Particularly useful effector groups are calichaemicin and derivatives thereof (see for example South African Patent Specifications Nos. 85/8794, 88/8127 and 90/2839).

Where it is desired to obtain a protein according to the invention linked to an effector or reporter molecule this may be prepared by standard chemical or recombinant DNA procedures in which the protein is linked either directly or via a coupling agent to the effector or reporter molecule. Particular chemical procedures include for example those described in International Patent Specification Nos. WO 93/06231, WO 92122583, WO 90/09195 and WO 89101476 and the Examples herein utilising functional groups e.g. thiols in the protein and where necessary appropriately activated effector or reporter molecules, for example thiol selective derivatives such as maleimides where the target Is a protein thiol group. Alternatively, where the effector or reporter molecule is a protein or polypeptide the linkage may be achieved using recombinant DNA procedures, for example as described herein or in International Patent Specification No. WO 86/01533 and European Patent Specification No. 392745.

The protein according to the invention may be useful in the detection or treatment of a number of diseases or disorders. Such diseases or disorders may include those described under the general headings of infectious disease, e.g. Viral infection; inflammatory disease/autoimmunity e.g. rheumatoid arthritis, osteoarthritis, inflammatory bowel disease; cancer, allergic/atopic disease e.g. asthma, eczema; congenital disease, e.g. cystic fibrosis, sickle cell anaemia; dermatologic disease, e.g. psoriasis; neurologic disease, e.g. multiple sclerosis; transplants e.g. organ transplant rejection, graft-versus-host disease; and metabolic) Idiopathic disease e.g. diabetes.

The proteins according to the invention may be formulated for use in therapy and/or diagnosis and according to a further aspect of the invention we provide a pharmaceutical composition comprising a protein according to the invention together with a pharmaceutically acceptable excipient, diluent or carrier. As explained above, the protein in this aspect of the invention may be optionally linked to one or more effector or reporter groups.

The pharmaceutical composition may take any suitable form for administration, and, preferably is in a form suitable for parenteral administration e.g. by injection or infusion, for example by bolus injection or continuous infusion. Where the composition is for injection of infusion, it may take the form of a suspension, solution or emulsion in an oily or aqueous vehicle and it may contain formulatory agents such as suspending, preservative, stabilising and/or dispersing agents.

Alternatively, the protein composition may be in dry form, for reconstitution before use with an appropriate sterile liquid.

If the protein composition is suitable for oral administration the formulation may contain, in addition to the active ingredient, additives such as starch, e.g. potato, maize or wheat starch, or cellulose or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the protein in a capsule which is insoluble in the gastric juices. It may also be preferable to include the protein or composition in a controlled release formulation.

If the protein composition is suitable for rectal administration the formulation may contain a binding and/or lubricating agent; for example polymeric glycols, gelatins, cocoa-butter or other vegetable waxes or fats.

Therapeutic and diagnostic uses of proteins according to the invention typically comprise administering an effective amount of the protein to a human subject. The exact amount to be administered will vary according to the use of the protein and on the age, sex and condition of the patient but may typically be varied from about 0.1 mg to 1000 mg for example from about 1 mg to 500 mg. The protein may be administered as a single dose or in a continuous manner over a period of time. Doses may be repeated as appropriate. Typical doses may be for example between 0.1–50 mg/kg body weight per single therapeutic dose, particularly between 0.1–20 mg/kg body weight for a single therapeutic dose.

The following Examples illustrate the invention. The following abbreviations are used:

AUC area under curve;
β-ME β-mercaptoethylamine;
DCM Di-Fab' Maleimide;
DTDP 4,4'dithiodipyridine;
Fab' antigen binding antibody fragment (with hinge);
F(ab')$_2$ dimeric Fab';
HC heavy chain;
LC light chain;
NEM N-ethylmaleimide;
PEG polyethylene glycol.

EXAMPLE 1

Evaluation of di-Fab' Production in *E. coli* Utilizing Different Hinge Sequences Strategy—To minimise any possible incorrect interchain disulphide bonds between hinge regions and any other cysteines the interchain disulphide bond was removed from all Fab' constructs. It had been shown previously that removal of the interchain disulphide bond of a di-Fab' did not affect the stability of the protein as judged by serum permanence times (ref. 9). PCR mutagenesis was used to change the interchain cysteines of cKappa and $C_H1$ to serines. This also enabled analysis of % di-Fab' formation by analysing periplasmic extracts on non-reducing SDS-PAGE, followed by heavy chain (HC) specific western blotting. This approach thereby allowed analysis of many constructs at the shake flask scale. Advantage was taken of the mutagenesis of $C_H1$ to introduce a SpeI restriction site to facilitate rapid cloning of novel hinge sequences as annealed oligonucleotide cassettes. To introduce this site the Ser N-terminal to the interchain disulphide Cys in the heavy chain was changed to a Thr, hence changing the C-terminus of the $C_H1$ from $^N$KSCDKTHTCAA$^C$ (SEQ ID NO:6) to $^N$K TSDKTHTCAA$^C$ (SEQ ID NO:7) (changes underlined).

Bacterial strain and plasmid constructions—All final expression plasmids were based on pACYC184 [Yarranton, G. T. and Mountain A. (1992) in: Protein Engineering—a Practical Approach (Rees, A R., Starnberg, M. J. E. and Wetzel, R. eds) IRL Press, Oxford pp. 303–326) and used to transform W3110, wild type *E. coli* ATCC 27325.

A variant of A5B7g3 Fab' (graft number 3 of a humanised Fab' binding to CEA—carcinoembryonic antigen) lacking the interchain disulphide bond was first constructed. The interchain Cys codon in the light chain (LC) cKappa was changed by PCR mutagenesis to Ser using the mutagenic oligo (SEQ ID NO:8): 5'-GCCGCG AATTCCGCACT-TCTCCCTCTAAGACTCTCCCCTGTT GAAGCTC-3'. A similar strategy was used to remove the interchain Cys codon from the $C_H1$ of the heavy chain (HC) and introduce the SpeI restriction site using the mutagenic oligo: 5'-CCGCAAGCTTGGATCCTCATCACGCGGCGCATGT GTGAGTTTTGTCACTAGTTT TGGGCTCAACTTTC-3' (SEQ ID NO:9) These and all subsequent clones were checked by DNA sequencing on an ABI 373A sequencer using PRISM cycle sequencing kit. Novel hinge sequences were produced by ligation of annealed oligonucleotide pairs with 5' SpeI-HindIII 3' ends via a similarly restricted A5B7g3 HC only plasmid, followed by reconstitution of the final dicistronic expression plasmid.

The coding region for Fab' 40.4 (a humanised Fab' binding a human cytokine) cKappa was similarly altered using the mutagenic oligonucleotide 5'-GGCCTGAGCTCACCAGTAACAAAAAGCTTTAAT AGAGGAGAGTCTTGAGGAGGAAAAAAAAAT GAAG-3' (SEQ ID NO:10). A restriction fragment for the original Fab' hinge ($^N$CAA$^C$) $C_H1$ lacking the interchain disulphide bond cysteine was moved from A5B7g3 into the expression plasmid for Fab 40.4 as a restriction fragment. Since the SpeI site in the Fab 40.4 final expression plasmid pDPH40 was unique it was possible to make further hinge variants rapidly by directly ligating annealed oligonucleotide pairs with 5' SpeI-NotI 3' overhangs into similarly restricted pDPH40. Details of the hinge sequences and plasmids are shown in Table I. During DNA manipulation steps preferred codons for *E. coli* as defined by Wada, K. N. et al. *Nucleic Acids Res.* (1991) 19, 1981 were chosen.

Shake flask experiments—Shake flask experiments were conducted essentially as described previously except that these were single plasmid experiments and required Tetracycline at 10 μgml$^{-1}$ [Humphreys, D. P. et al., FEBS Lett. (1996), 380, 194]. L-Broth was used for all experiments with A5B7, and in order to give the highest possible cell density, 2xTY was used for those with Fab 40.4. Redox active compounds were added as solids to a final concentration of 1 mM when required. Samples were taken at 0, 1, 2, and 4 hours post-induction.

Fermentation—synthetic SM6 C media: (5.0 g/L (NH$_4$)$_2$ SO$_4$, 3.312 g/L Na$_2$H$_2$PO$_4$.H$_2$O, 3.870 g/L KCl, 1.0 g/L MgSO$_4$.7H$_2$O, 1.0 g/L Citrate, 4.00 g/l Citric acid, 0.05 g/L CaCl$_2$.6H$_2$O, 0.02 g/L ZnSO$_4$.4H$_2$O, 0.02 g/L MnSO$_4$.4H$_2$O, 0.005 g/L CuSO$_4$.5H$_2$O, 0.004 g/L CoSO$_4$.6H$_2$O, 0.0967 g/L FeCl$_3$.6H$_2$O, 0.0003 g/L H$_3$BO$_3$, 0.0002 g/L NaMoO$_4$). Glycerol was used as a carbon source at 3% (w/v) and MAZU was used as an antifoam at 0.02% (v/v). pH was controlled with 50% (v/v) NH$_4$OH. Fab' expression was induced by switching of the carbon source to lactose at 5% (w/w), cells were harvested 24–36 hours post-induction. Fab' yields were typically 100–150 mg/L.

Western blotting—Samples equivalent to 2l of periplasmic fractions were diluted 5 fold with dH$_2$O and boiled for 5 minutes in non-reducing SDS-PAGE loading buffer, before being electrophoresed on 4–20% Tris-glycine gels (Novex) at 125 v for 1.75 hours. The proteins were transferred to a PVDF membrane (Novex) for 2 hours at 100 mA. The membrane was blocked for 1 hour at room temperature with 50 ml per membrane of 'blocking buffer' (PBS/0.1% (v/v) Tween 20/2% (w/v) skimmed milk), before shaking at room temperature for 1 hour with 5 ml per membrane of anti Fd antibody (Sheep IgG anti Human IgG(Fd), ref. PC075, The Binding Site, Birmingham, U.K.) at 1/1000 (v/v) in 'antibody buffer' (PBS/0.1% (v/v) Tween 20/0.1% 'blocking buffer'). The membrane was washed extensively in PBS/0.1% (v/v) Tween 20, before shaking at room temperature for 1 hour with 5 ml per membrane of a donkey anti sheep HRP conjugated antibody (Rabbit F(ab')$_2$ anti Sheep IgG Fc fragment HRP conjugate, ref. 313-036-046, Jackson) at 1/1000 (v/v) in 'antibody buffer'. The membrane was washed extensively in PBS/0.1% (v/v) Tween 20, before development with DAB substrate (Pierce). Life size positive transparencies of blots were used for laser scanning densitometry on a Molecular Dynamics model 300A machine using ImageQuant software version 4.2 Di-Fab derived heavy chains (di-HC) separate from Fab derived HC (free HC) during electrophoresis. Quantitation of the relative intensities of the two easily identifiable bands gave an estimate of the % di-Fab formed. This assumes a relatively constant level of production of HC and its association with LC between different Fab' variants. The pTTO-1 derived plasmids used produce an excess of LC, and so free HC in the periplasm is undetectable (Shauna West, personal communication). Di-HC of proteins lacking the interchain disulphide migrate with a mobility similar to a purified Fab' standard with the interchain disulphide. The total absorbance of each peak was quantified, and the % of di-Fab in each sample was calculated thus: absorbance of di-HC band÷absorbance of di-HC band+absorbance of HC band.

Fab' purification—Periplasmic extracts were clarified by centrifugation at 25,000 g for 30 minutes, the pH was increased to 6.5 with 2.5M Tris, and applied to a ProteinG sepharose (GammaBind, Pharmacia Biotech) column pre-equilibrated with P.B.S. After washing with P.B.S. to remove unbound material, the Fab' related material was eluted by washing the column with 0.1M Glycine.Cl pH 2.7. The pH of the eluate was increased to neutral with 2.5M Tris for storage at 4° C. Fab' concentrations after purification were typically $\leq$0.2 mgml$^{-1}$.

Plasmids were constructed with two copies of the repeat sequence TCPPCPA with between 0 and 5 spacing residues, see pDPH30-35, Table I (Fab' construct nomenclature shows the number of middle hinge sequence repeats, followed by Roman numerals to show the number of spacingn residues, and whether the protein has or lacks the interchain disulphide bond forming cysteine. For example, dDPH34 expresses A5B7g3 hinge 2iv inter=graft 3 of A5B7 with two hinge repeats, spaced by four aminoacids and lacking the interchain disulphide bond. pDPH42 expresses Fab' 40.4 hinge 2o+Cys, has two hinge repeats, with no spacing residues and having the interchain disulphide bond). These were evaluated for their ability to form di-Fab's in shake flask cultures as judged by western blotting and compared against the hinge ½ and hinge 1 constructs. The results are shown in Table II.

Similar to that seen by others (ref. 7), the hinge ½ Fab' produced no detectable di-Fab' in shake flasks. 'hinge 1' and 'hinge 2o' produced a moderate amount of di-Fab' (7.3% and 4.8% respectively). These versions were then made in the more highly expressed Fab 40.4, to see if increasing the periplasmic protein concentration of these Fabs would effect both an increase in di-Fab' formation in vivo, and discriminate the relative merits of an increasing number of hinge repeats.

It was surprising to see that all of the A5B7 constructs with spacing residues between the hinge repeats produced no detectable di-Fab'. The increasing length and flexibilty of these spacing regions could allow the second copy of the hinge repeat to fold back and form intra-HC disulphide bonds, thereby masking the cysteines from forming the desired inter-HC disulphide bonds. Although it is difficult to prove this assumption directly, two new constructs were designed using Fab 40.4 with reduced spacing/flexibility by removing one (Ala) or two (Ala-Thr) of the endogenous spacing residues between the rigid polyproline II helixes. The results for these as shown in Table II were not favourable, so a Fab' 40.4 with three copies of the hinge, 'hinge 3o' was made The results show that an increase in the number of copies of hinge repeats result in a steady decrease in the % of di-Fab' produced. This decrease in % di-Fab' can be presumed to be due to increasing toxicity of the protein in the periplasm as the proteins become more cysteine rich. The decrease in % di-Fab' correlated with decreased cell viability post-Fab' induction as shown by lower peak O.D.$_{600}$'s and increased cell lysis at the later time points. The disulphide redox machinery in the E. coli periplasm is now well understood, but it is thought to be less well adapted to cope with proteins having complex disulphide arrangements than that of the endoplasmic reticulum (reviewed by Humphreys et al., 1996 ibid). It seems likely that complex hinges are not well tolerated.

Reduction of the spacing between two hinge repeats does not increase di-Fab' formation. 'Fab' 40.4 inter hinge 2$_{-1}$' shows decreased di-Fab' compared to the 'hinge 2o' variant (8.1%±4.3 compared to 25.1% 8.43—see Table II). 'Fab' 40.4 inter hinge 2$_{-2}$' shows 49.8%±16.78 di-Fab'. This figure suggests a high level of di-Fab' production. In fact this protein appears unable even to produce substantial amounts of full length Fab'; this is demonstrated by the increased number and intensity of proteolytic bands shown by western blot. Hence there is a small amount of di-Fab' which is high relative to the amount of Fab', but very little of either protein is produced relative to 'hinge 1' and 'hinge 2o'. It can be postulated that removing one or both of these spacing residues makes the hinge regions so inflexible that the cysteines are forced into a conformation that makes them proteolytically exposed or reactive to native E. coli proteins. Since the unmodified 1 hinge gave the greatest di-Fab' yield in vivo, it was decided to test other hinge isotypes for their effectiveness.

Effect of hinge isotype—True hinge sequences for the IgG2, 3, and 4 could not be created, but rather the middle hinge of each was fused onto the existing IgG1 upper hinge. The hinges created are therefore called IgG2 'like'. Since long cysteine rich hinges are poorly tolerated, only the CPRC and the first of the three repeating sequences of the IgG3 middle hinge were used. The prime superscript is used to show that this IgG3 sequence was truncated. These constructs were analysed in the same way previously, and the results are shown in Table II.

The IgG3' like hinge was poorly tolerated and so gave an artifactually high % di-Fab' measurement in the same way that hinge $2_{-2}$ did. The long IgG3 hinge is thought to be highly flexible [Brekke, O. H. et al (1995) Immunol. Today 16, 85] and this is responsible for some of the properties of this isotype. In the periplasm this length of exposed peptide is likely to be susceptible to proteolysis, and this may be the reason for the poor level of production of this protein. The IgG 2 like hinge produced a reasonable amount of di-Fab' (20.8%±3.58), but gave no increase over that seen before with the IgG 1 derivatives. A relative inability of the IgG 4 like Fab' to produce di-Fab' (8.63%±1.41) was oberved. There is only one amino acid difference between the IgG 4 like hinge and the IgG1 hinge–CPSP relative to CPPC respectively. The results are consistent with previous work (ref. 22, 23), which found that IgG 4 was less able to form inter-HC disulphide bonds than IgG1. The presence of a serine between the two cysteines may allow increased flexibility of the middle hinge, and thereby formation of intra-HC disulphides which block inter-HC disulphide formation.

Effect of IgM and IgA tailpieces—IgM and IgA both have 18 amino-acid C-terminal extensions called secretory tailpieces that are involved in their polymerisation. The penultimate residue for both tailpieces is a cysteine. This and other HC cysteines, along with non-covalent interactions are known to be involved in polymer formation, although the exact disulphide organisation is not completely understood [Davis, A. C. et al., (1989), EMBO J. 8, 2519 and Wiersma, E. J. and Shulman, M. J. (1995), J. Immunol. 154, 5265]. The tailpiece has been added to all four IgG isotypes and effected their polymerisation even in the absence of the additional HC cysteines and non-covalently interacting residues found in IgM and IgA [Smith, R. I. F. et al (1995) J. Immunol. 154, 2226]. The wild type and tailpiece sequences described by Sørensen, V. et al., (1996) J. Immunol. 156, 2858] were added to Fab' 40.4 containing a 'hinge 1' sequence. The 'hinge 1' sequence was chosen since it seemed possible that at least one free cysteine might be required to act as a mimic of $Cys^{414}$ of IgM to provide for tailpiece-HC, and one other to allow for direct inter-HC interactions such as thought to be provided for by $Cys^{337}$ of IgM. The sequences constructed in pDPH 50 and 51 are shown in Table I.

The Fab's were analysed by shake flask culture/western blotting for the presence of increased polymer formation. Although 'hinge 1' was known to give ~30% di-Fab' formation, it was found that the presence of either of the tailpieces completely abolished di-Fab' formation. No evidence was found for the formation of higher polymeric states as judged by western blots of non reducing native and SDS PAGE. It was assumed that the abolition of dimer formation inherent to 'hinge 1' was due to folding back of the tailpieces to form an intra-HC disulphide between the tailpiece Cys and one of those in the hinge. This seems quite possible as the tailpiece sequences are thought able to form one beta strand, allowing the tailpiece Cys to be close to the hinge [Pumphrey, R. (1986) Immunol. Today 7, 174].

In general, the results show that the presence of extra hinge cysteines above the single one found in the original Fab' was the most important factor in promoting di-Fab' formation in vivo, with 'Hinge 1' and 'hinge 2o' being the best sequences. No benefit was found with other versions of the 1 hinge over these, nor with any of the other 3 IgG isotypes tested. Simple hinges proved to be the most useful, with increasing length of hinge producing less % di-Fab' and a higher cell mortality. This was seen both with increasing copy number of the IgG1 hinge sequence i.e. hinge 1, 2o, and 3o, and with the long and flexible truncated IgG3.

More subtle structural differences also affected the efficiency of di-Fab' formation in vivo. Manipulation of the spacing residues between two copies of the hinge sequence $^N$TCPPCPA$^{C\prime}$ (SEQ ID NO:11) implied the importance of conformation for maintaining the hinge cysteines in a di-Fab' forming state. If the spacing region became too long, di-Fab' formation was completely abolished, presumably by looping back of the hinge masking hinge cysteines, whilst if the spacing was too short, the hinge was badly degrading in vivo.

Previous reports found variable production of di-Fab' from high cell density fermentaion of 5–70% using the hinge sequence $^N$CPPCPPCPP$^C$ (SEQ ID NO:12) (ref. 9). The results herein demonstrate that it is very difficult to produce greater than 5–10% di-Fab' in vivo from fermentations and that this is reproducible. In addition to the hinge sequence, these differences may be accounted for by differences in Fab' expression levels, fermentation conditions and host strain. The Fab' yield here was 5 to 10 fold lower than that described by Rodrigues et al., (ref. 9). However, it is known that specific conditions can cause a spontaneous, high efficiency (~80%), and batch specific di-Fab' formation during purification. Such protein purification conditions were not used during these small scale experiments.

In summary, di-Fab' formation in vivo in the periplasm of E. coli is an inefficient process than is modulated inter alia by hinge sequence and complexity. Two hinge sequences ('hinge 1' and 'hinge 2o') have been identified under in vivo selection conditions to be the most efficient for di-Fab' formation.

EXAMPLE 2

Investigation of serum permanence times and hinge specific pegylation of F(ab')$_2$ molecules with modified hinges Reagents NEM, β-ME, DTDP, and Tris were from Sigma (UK) and of the highest grade available. Pyrogen free 'Flowfusor' water was used for chromatography (Fresenius, Basingstoke, UK). All other laboratory reagents were reagent grade from BDH (UK).

Production and Purification of Fab'

The Fab' used was 'Fab' 40.4', as described in Example 1. Fab' fermentations and Protein G sepharose purifications (GammaBind Plus, Pharmacia Biotech) were as described in Example 1, with one modification. E. coli periplasmic proteins were extracted from fermentation cell paste by overnight incubation at 30° C. and with shaking at 250 rpm in one fermentation harvest volume of 100 mM Tris/10 mM EDTA (pH 7.4). The conductivity and pH of the crude extract were altered to <3.5 mS cm$^{-1}$ and ≤4.5 by addition of water and glacial acetic acid respectively. Crude extract was then passed over an 80 ml (compacted) bed volume of Streamline SP cation exchange resin (Pharmacia Biotech) in expanded bed mode. The resin was pre-equilibrated with 50 mM sodium acetate pH 4.5 in expanded bed mode. After extensive washing, bound material was eluted in compacted mode with 50 mM sodium acetate/200 mM NaCl pH 4.5.

The pH of the peak fraction was increased to ≧6.5 with 2.5M Tris, and applied to a Protein G sepharose column pre-equilibrated with PBS. After washing with PBS to remove unbound material, the Fab' material was eluted with 0.1M Glycine Cl pH 2.7. The eluate was neutralised with 2.5M Tris for storage at 4° C.

Production and Purification of F(ab')$_2$

Fab' material was concentrated and buffer exchanged to ≧12 mgml$^{-1}$ in 0.1M sodium phosphate buffer pH 8.0 using ultra-filtration with a 10 kDa cut-off membrane. Hinge thiols were activated and traces of F(ab')$_2$ depending upon final protein concentration) were removed by reduction with 9-mM β-ME in 0.1M sodium phosphate buffer pH 8.0 for 45 min. at 37° C. Reductant was removed by desalting on a G25M sephadex column (PD10), (Pharmacia Biotech) pre-equilibrated with 0.1M sodium phosphate buffer pH 8.0. F(ab')$_2$ was allowed to form by incubation at room temperature overnight. Any remaining thiol groups were blocked by incubation with 10 mM NEM in PBS before analysis by SDS-PAGE (4–20% Tris/glycine gels, Novex UK) and HPLC (GF-250 column equilibrated with 0.2M sodium phosphate buffer pH 7.0).

F(ab')$_2$ was separated from Fab' on a small scale by collecting preparative HPLC fractions (GF-250XL column equilibrated with 0.2M sodium phosphate buffer pH 7.0), or on a large scale using hydrophobic interaction chromatography (HIC). Solid $(NH_4)_2SO_4$ was added to Fab'/F(ab')$_2$ mixtures to 0.75M before loading onto a phenyl-sepharose HP column (Pharmacia Biotech) equilibrated with 50 mM phosphate buffer pH 7.0/0.75M $(NH_4)_2SO_4$. After washing with equilibration buffer, bound material was eluted with 50 mM sodium phosphate buffer pH 7.0. The dimeric species has a higher affinity for the HIC matrix than the monomeric Fab'. All purified F(ab')$_2$ was judged to be 100% F(ab')$_2$ by HPLC and ≧95% F(ab')$_2$ by Coomassie stained SDS-PAGE.

Production of chemically cross linked F(ab')$_2$ (DFM)

DFM was produced as described previously using 1,6-bismaleimido-hexane (BMH) cross-linker (ref. 2).

Resistance to reduction of F(ab')$_2$

Purified F(ab')$_2$ at 0.25 mgml$^{-1}$ in 0.1M phosphate pH 7.0 was treated with β-ME from 0 to 2 mM for 45 min at 37° C. Reductions were stopped by addition of NEM to 10 mM and the relative amounts of F(ab')$_2$ and Fab' calculated by HPLC analysis.

Partial reduction of 'Hinge 2o' F(ab')$_2$ for hinge specific modification

Purified F(ab')$_2$ at 6 mgml$^{-1}$ in 0.1M phosphate pH 6.0 was treated with β-ME from 0 to 2 mM for 45 min. at 37° C. The reductant was removed by desalting with a P6 Biospin column (BioRad, UK) and samples taken immediately for thiol assay, NEM quenching and HPLC analysis and modification. 1.3 mM β-ME was used for all preparative partial reductions.

Production and Catin Exchange Purification of F(ab')$_2$

PEG-F(ab')$_2$ partially reduced as above was mixed with an equal volume of 25 kDa linear PEG-maleimide in 0.1M phosphate pH6.0 (Shearwater Polymers Inc, Birmingham, Ala., USA) to give a final molar excess of PEG:F(ab')$_2$ of 30 fold. After reacting overnight at room temperature, F(ab')$_2$-PEG was separated from the bulk of remaining F(ab')$_2$ using preparative scale HPLC. After concentration, and buffer exchange using a PD 10 column to 50 mM sodium acetate pH 4.5, the F(ab')$_2$-PEG/unreacted PEG fraction was loaded on to a 1.6 ml bed volume Poros HS column (PerSeptive Biosystems, Hertford, UK) on a BioCad Vision workstation. After washing with 5 column volumes to remove unbound PEG-maleimide, F(ab')$_2$ was removed from the column with a linear gradient of 50 mM sodium acetate pH 4.5 with NaCl from 40 mM to 1M. Fractions were concentrated and buffer exchanged to 0.2M sodium-phosphate buffer pH 7.0 before estimating protein concentrations using $A_{280}$. Protein was analysed by SDS-PAGE ujsing 4–12% Tris-MES gels (Novex, UK).

Thiol assay

Thiols per F(ab')$_2$ were determined using DTDP as described previously (ref. 17).

Iodination of F(ab')$_2$

300 μg of F(ab')$_2$ per animal group was $^{125}$I-labelled using Bolton and Hunter reagent (Amersham) to a specific activity of 0.22–0.33 μCi/μg.

Mass Spectrometry

Molecular masses for Fab' was determined used Fisons VG Quattro triple quadrupole equipment in electrospray ionisation mode.

Animal studies

Male Sprague Dawley rats of 220–250 g (Harlan) were injected intra venously with 20 μg $^{125}$I-labelled Fab 40,4 F(ab')$_2$ hinge variants whilst under Halothane anaesthesia (n=6 per group, except for 'hinge 2o' where n=10). Serial arterial bleeds from the tail were taken at 0.5, 2, 4, 6, 24, 48, 72 and 144 hours post administration. Samples were counted using a COBRA™ Autogamma counter (Canberra Packard). Data were plotted and Area Under Curve were calculated using GraphPad Prism (GraphPad Software Incorporated) and is expressed as % injected dose hour (% id.hr). the t½β is defined by time points 24, 48, 72. The means and standard errors of means (SEM) of data are shown.

RESULTS

Production of F(ab')$_2$ in vitro

Three hinge sequences were used to produce F(ab')$_2$ in vitro: 'hinge ½'=$^N$THTCAAC (SEQ ID NO:13); 'hinge 1'=$^N$THTCPPCPA$^C$ (SEQ ID NO:14); and 'hinge 2o'= $^N$THTCPPCPATCPPCPA$^C$ (SEQ ID NO:15). These contain 1, 2 and 4 hinge cysteines respectively. The 'hinge 1' and 'hinge 2o'proteins also contain one amino acid difference over 'hinge ½' of a Ser to Thr change in the C-terminus of $C_H1$ as described in Example 1.

After purification and concentration at pH 8.0 the Fab's were found to contain significant amounts of F(ab')$_2$. In order for the F(ab')$_2$ product to be as homogeneous as possible the Fab' preparations were subjected to identical strongly reducing conditions (80 mM β-ME, pH 8.0) so that the oxidation process started from 100% Fab'. Antigen binding analysis (BIAcore) of F(ab')$_2$ show that these very strong reducing conditions do not affect Fab affinity for soluble antigen. Reduced and desalted Fab' was left at room temperature overnight for maximum F(ab')$_2$ yield. However, by taking samples during the oxidation for quenching with NEM it could be seen that aprproximately 60% of achievable F(ab')$_2$ forms within the first 60 minutes of the oxidation—see FIG. 1. Both 'hinge ½' and 'hinge 2o' reached similar final yields of ~65% with an overnight incubation, however, F(ab')$_2$ formation within the first 30 minutes was more rapid for 'hinge 2o' than 'hinge ½'. This is probably a consequence of the greater number of hinge cysteines increasing the chances of Fab'—Fab' hinge cysteine interactions occurring. The yield of F(ab')$_2$ using 'hinge 2o' can be increased to 80% simply by increasing the concentration of Fab' to ≧20 mgml$^{-1}$.

It was surprising that 'hinge 1' did not reach the same final yields of F(ab')$_2$ formation as the other two proteins. It is possible that after reduction a percentage of 'hinge 1' rapidly undergoes intra-hinge disulphide formation, thereby capping the thiols off from inter-hinge disulphide formation.

No C-terminal proteolysis was observed with purified 'hinge 1' or hinge 2o' F(ab')$_2$, removing the possibility that a proportion of 'hinge' molecules have a cysteine missing. HC from reduction of both 'hinge 1' and 'hinge 2o' were shown by mass spectrometry to be full length molecules— 'hinge 1' had an observed mass of 24703.65±0.55 Da relative to the predicted mass of 24705.12 Da, 'hinge 2o' had an observed mass of 25366.40±6.13 Da relative to the predicted mass of 25374.88 Da.

Number of disulphide bonds in F(ab')$_2$ hinge regions

'Hinge ½' F(ab')$_2$ has an advantage over 'hinge 1' and 'hinge 2o' in that the product of hinge disulphide bond formation is homogeneous. In contrast 'hinge 1' may be able to form three different species of F(ab')$_2$ with a mixture of single and double disulphide and 'head to head' and 'head to tail' species (see FIG. 2). The picture is potentially even more complex with 'hinge 2o'. Consideration of the primary sequence (in the absence of modelling predictions) shows a large number of species that could be formed. These differ in the number of disulphide bonds (between one and four), staggered linear arrangements, and gross quaternary structure (both 'head to head' and 'head to tail' formations). Rotation around a disulphide bond makes it seem unlikely that single disulphide bonded forms of 'hinge 2o' could survive more than transiently in the absence of thiol capping agents.

With F(ab')$_2$ produced in vivo in E. coli, the presence of more hinge cysteines does not result per se in a highly disulphide bonded hinge (ref. 9). Hence it was important to demonstrate whether the two larger hinges contained more than one disulphide bond. Advantage was taken of an observation made whilst optimising reduction/oxidation conditions that 'hinge 2o' required a higher β-ME concentration in order to reduce all of the contaminating F(ab')$_2$ in the purified Fab'. It was possible that the different purified F(ab')$_2$ proteins would exhibit differences in their ability to resist reduction to Fab'. It was found that at 0.25 mgml$^{-1}$ and pH 7.0 'hinge ½' is completely reduced by 125 μM β-ME (see FIG. 3). At the same concentration of β-ME 68.3% of the 'hinge 1' preparation is still dimeric. This implies that approximately 68% of the population of 'hinge 1' F(ab')$_2$ has two disulphide bonds. At the slightly greater β-ME concentration of 166 μM, 100% of the 'hinge 2o' preparation is still dimeric. Hence by extrapolation, >68% of 'hinge 2o' molecules must have more than 2 disulphide bonds i.e. 3 or 4. Although hinge structural differences might have an effect on the accessibility or chemical reactivity of hinge disulphides, it seems unlikely that they would be significant enough to cause the gross differences seen in FIG. 3. Hence 'hinge 1' and 'hinge 2o' have a high degree of multiple disulphide bonding.

Effect of hinge sequence of F(ab')$_2$ pharmacokinetics in Rat

F(ab')$_2$ made from all three hinge constructs along with a DFM control were $^{125}$I-labelled so that their pharmacokinetics could be followed in a rat model. The data shown in Table III support the comparisons made in vitro between hinges ½, 1, and 2o. F(ab')$_2$ with a single hinge disulphide 'hinge ½' is cleared most rapidly from the circulation, with an AUC of 166.2±9.8% injected dose. hour (% id.hr). F(ab')$_2$ with an identical protein sequence, but linked by thioether bonds is cleared more slowly, AUC=384.2±32.1 (% id.hr). This is interpreted as evidence of the greater lability of the disulphide over thioether linkage, leading to a more rapid breakdown in vivo to Fab'. The smaller Fab' is excreted more rapidly through the kidneys than F(ab')$_2$. Increase of the average number of disulphide bonds in the hinge with 'hinge 1' and 'hinge 2o' results in increased AUC (423.6±35.0 and 509.7±31.3 (%id.hr) respectively) over that of 'hinge ½'. The curves for clearance from circulation of rats for the four F(ab')$_2$ molecules tested are shown in FIG. 4. This demonstrates graphically that the major effect of the different hinge stabilities appears to be on the α-phase. The initial clearance of 'hinge ½' F(ab')$_2$ is much more rapid than the other three F(ab')$_2$ molecules which are more grouped together. Presumably increased resistance of 'hinge 1', 'hinge 2o' and DFM F(ab')$_2$ to reductive or proteolytic forces in circulating blood leads to the molecules surviving for longer as the larger F(ab')$_2$ species which is cleared more slowly from the circulation.

Partial Reduction and PEGylation of 'Hinge 2o' F(ab')$_2$ in vitro

Since the 'hinge 2o' F(ab')$_2$ has a large proportion of molecules with multiple hinge disulphides, it seemed possible that a number of disulphide bonds could be broken and uncoupled thiols activated whilst retaining the molecule as a dimeric species. Such thiols would be particularly useful for attachment of effector or reporter groups such as radionucleotides, toxins, or PEG. Covalent attachment of PEG to proteins is attractive since it is a simple route to increasing the serum permanence, reducing immunogenicity, and decreasing proteolysis in vivo.

Using a range of β-ME concentrations at pH 6.0 and analysis of NEM quenched samples of HMPC it was found that at ≦1.8 mM β-ME 100% of the F(ab')$_2$ population remained dimeric. This figure may vary between batches of F(ab')$_2$ due to hinge disulphide occupancy heterogeneity. At 1.3 mM β-ME thiol assay with DTDP showed 1.034±0.090 thiols per F(ab')$_2$ being liberated for reaction. F(ab')$_2$ not treated with β-ME showed little free thiols per F(ab')$_2$. The efficiency of PEGylation of F(ab')$_2$ was calculated after purification of F(ab')$_2$-PEG by cation exchange and estimation of protein concentration by $A_{280}$ to be ≦1.3%.

TABLE I

Oligonucleotide cassettes for construction of hinge sequences.

Plasmid name and oligonucleotide cassette and hinge sequence

```
pDPH28 A5B7g3 hinge ½ Δinter
5' ACT AGT GAC AAA ACT CAC ACA TGC GCC GCG TGA TGA GGA TCC AAG CTT              3'          (SEQ ID NO.:16)
                                                                                             (SEQ ID NO.:10)
   T   S   D   K   T   H   T   C   A   A   * pDPH29 A5B7g3 hinge 1 Δinter
5' CT AGT GAC AAA ACT CAC ACC TGC CCG CCG TGA TGA GGA TCC A          3'                      (SEQ ID NO.:19)
3'    CA CTG TTT TGA GTG TGG ACG GGC GGC ACT ACT CCT AGG TTC GA 5'                           (SEQ ID NO.:21)
      T   S   D   K   T   H   T   C   P   P   * pDPH30 A5B7g3 hinge 2o Δinter
5' CT AGT GAC AAA ACT CAC ACC TGC CCG CCG TGC CCG CCG TGA TGA GGA TCC A          3'          (SEQ ID NO.:30)
3'    CA CTG TTT TGA GTG TGG ACG GGC GGC ACG GGC GGC ACT ACT CCT AGG TTC GA 5'
      T   S   D   K   T   H   T   C   P   P   C   P   P   * pDPH31 A5B7g3 hinge 2i Δinter
5' CT AGT GAC AAA ACT CAC ACC TGC CCG CCG ACC TGC CCG CCG TGA TGA GGA TCC A          3'      (SEQ ID NO.:24)
3'    CA CTG TTT TGA GTG TGG ACG GGC GGC TGG ACG GGC GGC ACT ACT CCT AGG TTC GA 5'
      T   S   D   K   T   H   T   C   P   P   T   C   P   P   * pDPH32 A5B7g3 hinge 2ii Δinter
5' CT AGT GAC AAA ACT CAC ACC TGC CCG CCG GGA ACC TGC CCG CCG TGA TGA GGA TCC A          3'  (SEQ ID NO.:25)
3'    CA CTG TTT TGA GTG TGG ACG GGC GGC CCT TGG ACG GGC GGC ACT ACT CCT AGG TTC GA 5'
      T   S   D   K   T   H   T   C   P   P   G   T   C   P   P   * pDPH33 A5B7g3 hinge 2iii Δinter
5' CT AGT GAC AAA ACT CAC ACC TGC CCG CCG GGA GGA ACC TGC CCG CCG TGA TGA GGA TCC A          3'   (SEQ ID NO.:26)
3'    CA CTG TTT TGA GTG TGG ACG GGC GGC CCT CCT TGG ACG GGC GGC ACT ACT CCT AGG TTC GA 5'
      T   S   D   K   T   H   T   C   P   P   G   G   T   C   P   P   * pDPH34 A5B7g3 hinge 2iv Δinter
5' CT AGT GAC AAA ACT CAC ACC TGC CCG CCG GGA GGA GGA ACC TGC CCG CCG TGA TGA GGA TCC A          3'   (SEQ ID NO.:27)
3'    CA CTG TTT TGA GTG TGG ACG GGC GGC CCT CCT CCT TGG ACG GGC GGC ACT ACT CCT AGG TTC GA 5'
      T   S   D   K   T   H   T   C   P   P   G   G   G   T   C   P   P   * pDPH35 A5B7g3 hinge 2v Δinter
5' CT AGT GAC AAA ACT CAC ACC TGC CCG CCG GGA GGA GGA GGA AAA GGA GAA ACC TGC CCG CCG TGA TGA GGA TCC A   3'   (SEQ ID NO.:28)
3'    CA CTG TTT TGA GTG TGG ACG GGC GGC CCT CCT CCT CCT TTT CCG CTT TGG ACG GGC GGC ACT ACT CCT AGG TTC GA 5'
      T   S   D   K   T   H   T   C   P   P   G   G   G   G   K   G   E   T   C   P   P   * pDPH40 Fab 40.4 hinge ½ Δinter
5' CT AGT GAC AAA ACT CAC ACA TGC GCC GCG TGA TGA GGA TCC AAG CTT GC              3'           (SEQ ID NO.:29)
3'    CA CTG TTT TGA GTG TGT ACG CGG CGC ACT ACT CCT AGG TTC GAA CGG 5'                        (SEQ ID NO.:30)
      T   S   D   K   T   H   T   C   A   A   * pDPH41 Fab 40.4 hinge 2o Δinter
5' CT AGT GAC AAA ACT CAC ACA TGC CCG CCG ACC TGC CCG CCG TGA TGA GGA TCC A          3'        (SEQ ID NO.:31)
3'    CA CTG TTT TGA GTG TGT ACG GGC GGC TGG ACG GGC GGC ACT ACT CCT AGG TTC GA 5'             (SEQ ID NO.:32)
      T   S   D   K   T   H   T   C   P   P   T   C   P   P   *
``` pDPH... (continued)

```
                                                                                             (SEQ ID NO.:33)
                                                                                             (SEQ ID NO.:34)

(SEQ ID NO.:17)
                                                                                             (SEQ ID NO.:10)

(SEQ ID NO.:23)
```

TABLE I-continued

Oligonucleotide cassettes for construction of hinge sequences.

Plasmid name and oligonucleotide cassette and hinge sequence

```
              T   S   D   K   T   H   T   C   P   P   C   P   A   T   C   P   P   C   P   P   C   P   A   *
pDPH42 Fab 40.4 hinge 2o +Cys
5' ACT TGT GAC AAA ACT CAC ACA TGC CCG CCG TGC CCG GCG ACC TGC CCG CCG TGC CCG CCG TGC CCG GCG TGA TGA GGA TCC A 3'
              T   C   D   K   T   H   T   C   P   P   C   P   A   T   C   P   P   C   P   P   C   P   A   *
```
(SEQ ID NO.:24)

(SEQ ID NO.:53)
(SEQ ID NO.:54)

```
pDPH44 Fab 40.4 hinge 1 Δinter
5' CT AGT GAC AAA ACT CAC ACA TGC CCG CCG TGC CCG GCG TGA TGA GGA TCC A 3'
3'    A CTG TTT TGA GTG TGT ACG GGC GGC ACG GGC CGC ACT CCT AGG TTC GA 5'
              T   S   D   K   T   H   T   C   P   P   C   P   A   *
```
(SEQ ID NO.:20)
(SEQ ID NO.:21)

```
pDPH52 Fab 40.4 hinge 1=Cys
5' ACT TGT GAC AAA ACT CAC ACA TGC CCG CCGTGC CCG CCG TGA GGA TCC A 3'
              T   C   D   K   T   H   T   C   P   C   P   P   *
```
(SEQ ID NO.:51)
(SEQ ID NO.:52)

```
pDPH53 Fab 40.4 hinge 2₋₁ Δinter
5' CT AGT GAC AAA ACT CAC ACA TGC CCG CCG TGC ACC CCG GCG ACC TGC CCG CCG TGA GGA TCC A 3'
3'    A CTG TTT TGA GTG TGT ACG GGC GGC ACG TGG GGC CGC TGG ACG GGC GGC ACT CCT AGG TTC GA 5'
              T   S   D   K   T   H   T   C   P   P   C   T   P   A   T   C   P   P   *
```
(SEQ ID NO.:35)
(SEQ ID NO.:36)

```
pDPH54 Fab 40.4 hinge 2₋₂ Δinter
5' CT AGT GAC AAA ACT CAC ACA TGC CCG CCG TGC CCG GCG ACC TGC CCG CCG TGA GGA TCC A 3'
3'    A CTG TTT TGA GTG TGT ACG GGC GGC ACG GGC CGC TGG ACG GGC GGC ACT CCT AGG TTC GA 5'
              T   S   D   K   T   H   T   C   P   P   C   P   A   T   C   P   P   *
```
(SEQ ID NO.:37)
(SEQ ID NO.:38)

```
pDPH69 Fab 40.4 hinge 3o Δinter
5' CT AGT GAC AAA ACT CAC ACA TGC CCG CCG TGC CCG GCG ACC TGC CCG CCG TGC CCG GCG ACC TGC CCG CCG TGA TGA TCC AGG
3' CA CTG TTT TGA GTG TGT ACG GGC GGC ACG GGC CGC TGG ACG GGC GGC ACG GGC CGC TGG ACG GGC GGC ACT ACT AGG
              S   D   K   T   H   T   C   P   P   C   P   A   T   C   P   P   C   P   A   T   C   P   P   A
              AAG CTT GC 3'
              TTC GAA CGC CGG 5'
```
(SEQ ID NO.:40)
(SEQ ID NO.:39)

```
pDPH50 Fab 40.4 hinge 1 Δinter IgMtp
5' CT AGT GAC AAA ACT CAC ACC TGC CCG CCG TGC GCG GCG AAA ACC GTG ACC CTG TAT AAC AGC GAT ACC GCG GGC ACC
3'    A CTG TTT TGA GTG TGG ACG GGC GGC ACG CGC CGC TTT TGG CAC TGG GAC ATA TTG TCG CTA TGG CGC CCG TGG
              T   S   D   K   T   H   T   C   P   P   C   A   A   K   P   T   L   Y   N   S   D   T   A   G   T
              TGT TAT TGA TGA GGA TCC AAG CTT GC 3'
              ACA ATA ACT ACT CCT AGG TTC GAA CGC CGG 5'
              C   Y   *   *
```
(SEQ ID NO.:41)
(SEQ ID NO.:42)

```
pDPH51 Fab 40.4 hinge 1 Δinter IgAtp
5' CT AGT GAC AAA ACT CAC ACC TGC CCG CCG TGC CCG GCG AAA CCG TGC CCG CCG TGC CCG GCG GAA GTG CAC CTG GAT GGC ACC
3' CA CTG TTT TGA GTG TGG ACG GGC GGC ACG CGG GGC GGC GGC TTT GGC GTA CAC TCG CAC GTG GAC CTA CCG TGG
              T   S   D   K   T   H   T   C   P   P   C   P   A   K   P   T   H   V   N   V   S   V   M   A   E   V   D   G   T
              TGT TAT TGA TGA GGA TCC AAG CTT GC 3'
              ACA ATA ACT ACT CCT AGG TTC GAA CGC CGG 5'
              C   Y   *   *
```
(SEQ ID NO.:43)
(SEQ ID NO.:44)

TABLE I-continued

Oligonucleotide cassettes for construction of hinge sequences.

Plasmid name and oligonucleotide cassette and hinge sequence pDPH61 Fab 40.4 'IgG2 like' hinge Δinter
5' CT AGT GAC AAA ACT CAC ACC TGC GTG GAA TGC CCG CCG TGC CCG GCG TGA TGA GGA TCC AAG CTT GC    3'    (SEQ ID NO.:45)
3'    A CTG TTT TGA GTG TGG ACG ACG CAC CTT ACG GGC GGC ACG GGC CGC ACT ACT CCT AGG TTC GAA CGC CGG 5'    (SEQ ID NO.:46)
     T  S   D   K   T   H   T   C   V   E   C   P   P   C   P   A   * pDPH62 Fab 40.4 'IgG3' like' hinge Δinter
5' CT AGT GAC AAA ACT CAC ACC TGC CCG CGT TGC CCG GAA CCG AAA AGC TGC GAT ACC CCG CCG TGC CCG CGT TGC CCG GCG TGA TGA TCC
3'    A CTG TTT TGA GTG TGG ACG GGC GCA ACG GGC CTT GGC TTT TCG ACG CTA TGG GGC GGC ACG GGC GCA ACG GGC CGC ACT ACT AGG
     T  S   D   K   T   H   T   C   P   R   C   P   E   P   K   S   C   D   T   P   P   C   P   R   C   P   A   *         (SEQ ID NO.:48)
                                                        AAG CTT GC    3'
                                                        TTC GAA CGC CGG 5'                                                   (SEQ. ID NO.:47)

pDPH63 Fab 40.4 'IgG4 like' hinge Δinter
5' CT AGT GAC AAA ACT CAC ACC TGC CCG AGC TGC CCG GCG CCG GAA TTC CTT GGC    3'    (SEQ ID NO.:49)
3'    A CTG TTT TGA GTG TGG ACG GGC TCG ACG GGC CGC GGC CTT AAG GAA CGC CGG 5'    (SEQ ID NO.:50)
     T  S   D   K   T   H   T   C   P   S   C   P   A   *

TABLE II

Effect of hinge sequences on efficiency of di-Fab formation in vivo in shake flask experiments.

| | | % di-HC |
|---|---|---|
| A5B7 Δinter, hinge ½ | TSDKTHTCAA (SEQ ID NO: 18) | Non det. |
| A5B7 Δinter, hinge 1 | TSDKTHTCPPCA (SEQ ID NO:21) | 7.375 ± 2.338 |
| A5B7 Δinter, hinge 2o | TSDKTHTCPPCPATCPPCPA (SEQ ID NO:55) | 4.804 ± 3.23 |
| A5B7 Δinter, hinge 2i | TSDKTHTCPPCPAGTCPPCPA (SEQ ID NO:24) | Non det. |
| A5B7 Δinter, hinge 2ii | TSDKTHTCPPCPAGGTCPPCPA (SEQ ID NO:28) | Non det. |
| A5B7 Δinter, hinge 2iii | TSDKTHTCPPCPAGGGTCPPCPA (SEQ ID NO:30) | Non det. |
| A5B7 Δinter, hinge 2iv | TSDKTHTCPPCPAGGGGTCPPCPA (SEQ ID NO:32) | Non det. |
| A5B7 Δinter, hinge 2v | TSDKTHTCPPCPAKGKGETCPPCPA (SEQ ID NO:34) | Non det. |
| Fab 40.4 Δinter, hinge ½ | TSDKTHTCAA (SEQ ID NO:18) | Non det. |
| Fab 40.4 Δinter, hinge 1 | TSDKTHTCPPCA (SEQ ID NO:21) | 35.7 ± 4.85 |
| Fab 40.4 Δinter, hinge 2o | TSDKTHTCPPCPATCPPCPA (SEQ ID NO:55) | 25.1 ± 8.43 |
| Fab 40.4 Δinter, hinge 3o | TSDKTHTCPPCPATCPPCPATCPPCPA (SEQ ID NO:40) | 20.8 ± 3.58 |
| Fab 40.4 Δinter, hinge 2$_{-1}$ | TSDKTHTCPPCPTCPPCPA (SEQ ID NO:36) | 8.1 ± 4.3 |
| Fab 40.4 Δinter, hinge 2$_{-2}$ | TSDKTHTCPPCPCPPCPA (SEQ ID NO:38) | 49.8 ± 16.78 |
| Fab 40.4 hinge 1 + Cys | TCDKTHTCPPCPA (SER ID NO:52) | 14.4 ± 9.75 |
| Fab 40.4 hinge 2o + Cys | TCDKTHTCPPCPATCPPCPA (SEQ ID NO:54) | 16.3 ± 2.30 |
| Fab 40.4 'IgG2 like' hinge Δinter | TSDKTHTCCVECPPCPA (SEQ ID NO:46) | 20.8 ± 5.95 |
| Fab 40.4 'IgG3' like' hinge Δinter | TSDKTHTCPRCPEPKSCDTPPPCPRCPA (SEQ ID NO:48) | 29.3 ± 5.95 |
| Fab 40.4 'IgG4 like' hinge Δinter | TSDKTHTCPSCPA (SEQ ID NO:50) | 8.63 ± 1.41 |

REFERENCES

1. Covell, D. G., J. Barbet., O. D. Holton., C D. V. Black., R. J. Parker, and J. N. Weinstein. 1986. Pharmacokinetics of monoclonal immunoglobulins G1, F(ab')$_2$, and Fab' in Mice. *Cancer Research* 46:3969.
2. King, D. J., A. Turner., A. P. H. Farnsworth., J. R. Adair., R. J. Owens., B. Pedley., D. Baldock., K. A. Proudfoot., A. D. G. Lawson., N. R. A. Beeley., K. Millar., T. A. Millican., B. A. Boyce., P. Antoniw., A. Mountain., R. H. J3. Begent., D. Shochat, and G. T. Yarranton. 1994. Improved tumour targeting with chemically cross-linked recombinant antibody fragments. *Cancer Research* 54:6176.
3. Kaku, S., S. Yano., T. Kawasaki., Y. Sakai., K. I. Suzuki., K. Kawamura., Y. Masuho., N. Satoh., T. Takenaka., N. F. Landolfi, and M. S. Co. 1996. Comparison of the anti-platelet agent potential of the whole molecule, F(ab')$_2$ and Fab fragments of humanized anti-GPIIb/IIIa monoclonal antibody in Monkeys. *General Pharmacology* 27:435.
4. Plückthun, A. 1992. Mono- and bivalent antibody fragments produced in *Escherichia coli*: engineering, folding and antigen binding. *Immunological Reviews* 130:151.
5. George, A. J. T, and A. Epenetos. 1996. Advances in antibody engineering. *Expert Opinion in Therapeutic Patents* 6:441.
6. Melton, R. G. 1996. Preparation and purification of antibody-enzyme conjugates for therapeutic applications. *Advanced Drug Delivery Reviews* 22:289.
7. Carter, P., R. F. Kelly., M. L. Rodrigues., B. Snedecor., M. Covarrubias., M. D. Velligan., W. L. T. Wong., A. M. Rowland., C. E. Kotts., M. E. Carver., M. Yang, and A. et al. 1992. High level *Escherichia coli* expression and production of a bivalent humanized antibody fragment. *Bio/Technology* 10:163.
8. Better, M., S. L. Bernhard., S. P. Lei., D. M. Fishwild., 3. A. Lane., S. F. Carroll, and A. H. Horwitz. 1993. Potent anti-CD5 ricin A chain immunoconjugates from bacterially produced Fab' and F(ab')$_2$. *Proceedings of the National Academy of Sciences, U.S.A.* 90:457.
9. Rodrigues, M. L., B. Snedecor., C. Chen., W. L. T. Wong., S. Garg., G. S. Blank., D. Maneval, and P. Carter. 1993. Engineering Fab' fragments for efficient F(ab')$_2$ formation in *Escherichia coli* and for improved in vivo stability. *Journal of Immunology* 12:6954.
10. Pack, P, and A. Plückthun. 1992. Miniantibodies: use of amphipathic helices to produce functional, flexibly linked dimeric Fv fragments with high avidity in *Escherichia coli*. *Biochemistry* 31:1579.
11. Ducancel, F., D. Gillet., A. Carrier., E. Lajeunesse., A. Menez, and J. C. Boulain. 1993. Recombinant colorimetric antibodies: construction and characterization of a bifunctional F(ab)$_2$/alkaline phosphate conjugate produced in *Escherichia coli*. *Bio/Technology* 11:601.
12. Speck, R. R., J. R. Couto., S. G. Godwin., R. B. Christian., R. Kiwan., R. L. Ceriani, and J. A. Peterson. 1996. Inverted Fab2s (IFab2s): engineering and expression of novel, dimeric molecules, with a molecular weight of 100 000. *Molecular Immunology* 33:1095.
13. Rheinnecker, M., C. Hardt., L. L. hag., P. Kufer., R. Gruber., A. Hoess., A. Lupas., C. Rottenberger., A. Pluckthun, and P. Pack. 1996. Multivalent antibody fragments with high functional affinity for a tumour-associated carbohydrate antigen. *Journal of Immunology* 157:2989.
14. Glennie, M. 3., H. M. McBride., A. T. Worth, and G. T. Stevenson. 1987. Preparation and performance of bispecific F(ab'y)$_2$ antibody containing thioetherlinked Faby fragments. *Journal of Immunology* 139:2367.
15. King, D. J., J. R. Adair., S. Angal., D. C. Low., K. A. Proudfoot., J. C. Lloyd., M. W. Bodmer, and G. T. Yarranton. 1992. Expression, purification and characterization of a mouse-human chimeric antibody and chimeric Fab' fragment. *Biochemical Journal* 281:317.
16. Worrell, N. R., A. J. Cucumber., G. D. Parnell., A. Mirza., J. A. Forrester, and W. C. J. Ross. 1986. Effect of linkage variation on pharmacokinetics of ricin A chain-antibody conjugates in normal rats. *Anti-Cancer Drug Design* 1:179.
17. Lyons, A., D. J. King., R. J. Owens., G. T. Yarranton., A. Millican., N. R. Whittle, and J. R. Adair. 1990. Site-specific attachment to recombinant antibodies via introduced surface cysteine residues. *Protein Engineering* 3:703.
18. Moroder, L., G. Hübener., S. Göhring-Romani., W. Göhring., H. J. Musiol, and E. Wünsch. 1990. Fully synthetic immunogens. Part I. Kinetic studies on air oxidation of the human IgGi bis-cysteinyl fragment 225–232. *Tetrahedron* 46:3305.
19. Harris, L. J., S. B. Larson., K. W. Hasel., 3. Day., A. Greenwood, and A. McPherson. 1992. The three-dimensional structure of an intact monoclonal antibody for canine lymphoma. *Nature* 360:369.
20. Burton, D. R, and J. M. Woof. 1992. Human antibody effector function. *Advances in Immunology* 51:1.
21. Buchegger, F., A. Pelegrin., N. Hardman., C. Heusser., 3. Lukas., W. Dolci, and J. P. Mach. 1992. Different behaviour of mouse-human chimeric antibody F(ab')$_2$ fragments of $IgG_1$, $IgG_2$, and $IgG_4$ sub-class in vivo. *International Journal of Cancer* 50:416.
22. Angal, S., D. J. King., M. W. Bodmer., A. Turner., A. D. G. Lawson., G. Roberts., B. Pedley, and J. R. Adair. 1993. A single amino acid substitution abolishes the heterogeneity of chimeric mouse/human (IgG4) antibody. *Molecular Immunology* 30:105.
23. Bloom, J. W., M. S. Madanat., D. Marriott., T. Wong, and S. Y. Chan. 1997. Intrachain disulfide bond in the core hinge region of human IgG4. *Protein Science* 6:407.
24. Yoshimori, T., T. Semba., H. Takemoto., S. Akagi., A. Yamamoto, and Y. Tashiro. 1990. Protein disulfide-isomerase in rat exocrine pancreatic cells is exported from the endoplasmic reticulum despite possessing the retention signal. *Journal of Biological Chemistry* 265:15984.

What is claimed is:

1. A peptide which functions as a hinge region in an antibody or antigen binding fragment thereof, or a protected or reactive derivative of the N-terminal amino group or the C-terminal carboxy group of said peptide, said peptide comprising the amino acid sequence set forth in SEQ ID NO:1, wherein the amino acid at position 7 of SEQ ID NO:1 and the amino acid at position 8 of SEQ ID NO:1 is each a neutral aliphatic L-amino acid residue.

2. A peptide according to claim 1 wherein the amino acid at position 7 of SEQ ID NO:1 is alanine.

3. A peptide according to claim 2 wherein the amino acid at position 8 of SEQ ID NO:1 is threonine.

4. A peptide according to claim 1 wherein the amino acid at position 8 of SEQ ID NO:1 is threonine.

5. An antibody or antigen binding fragment thereof comprising one polypeptide chain, wherein said polypeptide chain comprises the amino acid sequence set forth in SEQ ID NO:1, wherein the amino acid at position 7 of SEQ ID NO:1 and the amino acid at position 8 of SEQ ID NO:1 is each a neutral aliphatic L-amino acid residue.

6. An antibody or antigen binding fragment thereof comprising two polypeptide chains, wherein each of said polypeptide chains comprises the amino acid sequence set forth in SEQ ID NO:1, wherein the amino acid at position 7 of SEQ ID NO:1 and the amino acid at position 8 of SEQ ID NO:1 is each a neutral aliphatic L-amino acid residue, and wherein each of said polypeptide chains is covalently linked to the other through one, two, three or four of the cysteine residues present in SEQ ID NO:1.

7. An antibody or antigen binding fragment thereof of claim 5 which is a Fab or Fab' fragment.

8. An antibody or antigen binding fragment thereof of claim 5 which has one or more effector or reporter molecules attached to it.

9. An antibody or antigen binding fragment thereof of claim 6 which has one or more effector or reporter molecules attached to it.

10. An antibody or antigen binding fragment thereof of claim 7 which has one or more effector or reporter molecules attached to it.

* * * * *

SEQUENCE LISTING

```
<160> NUMBER OF SEQ ID NOS: 55

<210> SEQ ID NO 1
<211> LENGTH: 14
<212> TYPE: PRT
<213> ORGANISM: Artificial Sequence
<220> FEATURE:
<223> OTHER INFORMATION: fragment
<220> FEATURE:
<221> NAME/KEY: VARIANT
<222> LOCATION: (1)...(14)
<223> OTHER INFORMATION: Xaa = Any Amino Acid

<400> SEQUENCE: 1

Thr Cys Pro Pro Cys Pro Xaa Xaa Cys Pro Pro Cys Pro Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: fragment

<400> SEQUENCE: 2

Thr Cys Pro Pro Cys Pro Ala Thr Cys Pro Pro Cys Pro Ala
1               5                   10

<210> SEQ ID NO 3
<211> LENGTH: 36
<212> TYPE: PRT
<213> ORGANISM: Artificial Sequence
<220> FEATURE:
<223> OTHER INFORMATION: fragment
<220> FEATURE:
<221> NAME/KEY: VARIANT
<222> LOCATION: (1)...(36)
<223> OTHER INFORMATION: Xaa = Any Amino Acid

<400> SEQUENCE: 3

Thr His Arg Cys Tyr Ser Pro Arg Pro Arg Cys Tyr Ser Pro Arg Ala
1               5                   10                  15

Leu Ala Xaa Ala Ala Cys Tyr Ser Pro Arg Pro Arg Cys Tyr Ser Pro
            20                  25                  30
```

Arg Ala Leu Ala
        35

<210> SEQ ID NO 4
<211> LENGTH: 14
<212> TYPE: PRT
<213> ORGANISM: Artificial Sequence
<220> FEATURE:
<223> OTHER INFORMATION: fragment
<220> FEATURE:
<221> NAME/KEY: VARIANT
<222> LOCATION: (1)...(14)
<223> OTHER INFORMATION: Xaa = Any Amino Acid

<400> SEQUENCE: 4

Thr Cys Pro Pro Cys Pro Xaa Thr Cys Pro Pro Cys Pro Ala
 1               5                  10

<210> SEQ ID NO 5
<211> LENGTH: 42
<212> TYPE: DNA
<213> ORGANISM: Artificial Sequence
<220> FEATURE:
<223> OTHER INFORMATION: fragment

<400> SEQUENCE: 5
acatgcccgc cgtgcccggc gacctgcccg ccgtgcccgg cg                        42

<210> SEQ ID NO 6
<211> LENGTH: 11
<212> TYPE: PRT
<213> ORGANISM: Artificial Sequence
<220> FEATURE:
<223> OTHER INFORMATION: fragment

<400> SEQUENCE: 6

Lys Ser Cys Asp Lys Thr His Thr Cys Ala Ala
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: fragment

<400> SEQUENCE: 7

Lys Thr Ser Asp Lys Thr His Thr Cys Ala Ala
 1               5                  10

<210> SEQ ID NO 8
<211> LENGTH: 49
<212> TYPE: DNA
<213> ORGANISM: Artificial Sequence
<220> FEATURE:
<223> OTHER INFORMATION: fragment

<400> SEQUENCE: 8
gccgcgaatt ccgcacttct ccctctaaga ctctcccctg ttgaagctc                 49

<210> SEQ ID NO 9
<211> LENGTH: 67
<212> TYPE: DNA
<213> ORGANISM: Artificial Sequence
<220> FEATURE:
<223> OTHER INFORMATION: fragment

<400> SEQUENCE: 9

```
ggcctgagct caccagtaac aaaaagcttt aatagaggag agtcttgagg aggaaaaaaa      60
aatgaag                                                                67
```

<210> SEQ ID NO 10
<211> LENGTH: 68
<212> TYPE: DNA
<213> ORGANISM: Artificial Sequence
<220> FEATURE:
<223> OTHER INFORMATION: fragment

<400> SEQUENCE: 10

```
ccgcaagctt ggatcctcat cacgcggcgc atgtgtgagt tttgtcacta gttttgggct      60
caactttc                                                               68
```

<210> SEQ ID NO 11
<211> LENGTH: 7
<212> TYPE: PRT
<213> ORGANISM: Artificial Sequence
<220> FEATURE:
<223> OTHER INFORMATION: fragment

<400> SEQUENCE: 11

Thr Cys Pro Pro Cys Pro Ala
 1               5

<210> SEQ ID NO 12
<211> LENGTH: 9
<212> TYPE: PRT
<213> ORGANISM: Artificial Sequence
<220> FEATURE:
<223> OTHER INFORMATION: fragment

<400> SEQUENCE: 12

Cys Pro Pro Cys Pro Pro Cys Pro Pro
 1               5

<210> SEQ ID NO 13
<211> LENGTH: 6
<212> TYPE: PRT
<213> ORGANISM: Artificial Sequence
<220> FEATURE:
<223> OTHER INFORMATION: fragment

<400> SEQUENCE: 13

Thr His Thr Cys Ala Ala
 1               5

<210> SEQ ID NO 14
<211> LENGTH: 9
<212> TYPE: PRT
<213> ORGANISM: Artificial Sequence
<220> FEATURE:
<223> OTHER INFORMATION: fragment

<400> SEQUENCE: 14

Thr His Thr Cys Pro Pro Cys Pro Ala
 1               5

<210> SEQ ID NO 15
<211> LENGTH: 15
<212> TYPE: PRT
<213> ORGANISM: Artificial Sequence
<220> FEATURE:
<223> OTHER INFORMATION: fragment

```
<400> SEQUENCE: 15

Thr His Thr Cys Pro Pro Cys Pro Ala Thr Cys Pro Pro Cys Pro
  1               5                  10                  15

<210> SEQ ID NO 16
<211> LENGTH: 48
<212> TYPE: DNA
<213> ORGANISM: Artificial Sequence
<220> FEATURE:
<223> OTHER INFORMATION: fragment

<400> SEQUENCE: 16
actagtgaca aaactcacac atgcgccgcg tgatgaggat ccaagctt            48

<210> SEQ ID NO 17
<211> LENGTH: 53
<212> TYPE: DNA
<213> ORGANISM: Artificial Sequence
<220> FEATURE:
<223> OTHER INFORMATION: fragment

<400> SEQUENCE: 17
ctagtgacaa aactcacaca tgcgccgcgt gatgaggatc caagcttgcg gcc      53

<210> SEQ ID NO 18
<211> LENGTH: 10
<212> TYPE: PRT
<213> ORGANISM: Artificial Sequence
<220> FEATURE:
<223> OTHER INFORMATION: fragment

<400> SEQUENCE: 18

Thr Ser Asp Lys Thr His Thr Cys Ala Ala
  1               5                  10

<210> SEQ ID NO 19
<211> LENGTH: 55
<212> TYPE: DNA
<213> ORGANISM: Artificial Sequence
<220> FEATURE:
<223> OTHER INFORMATION: fragment

<400> SEQUENCE: 19
ctagtgacaa aactcacacc tgcccgccgt gcccggcgtg atgaggatcc aagct    55

<210> SEQ ID NO 20
<211> LENGTH: 55
<212> TYPE: DNA
<213> ORGANISM: Artificial Sequence
<220> FEATURE:
<223> OTHER INFORMATION: fragment

<400> SEQUENCE: 20
ctagtgacaa aactcacaca tgcccgccgt gcccggcgtg atgaggatcc aagct    55

<210> SEQ ID NO 21
<211> LENGTH: 13
<212> TYPE: PRT
<213> ORGANISM: Artificial Sequence
<220> FEATURE:
<223> OTHER INFORMATION: fragment

<400> SEQUENCE: 21

Thr Ser Asp Lys Thr His Thr Cys Pro Pro Cys Pro Ala
  1               5                  10
```

```
<210> SEQ ID NO 22
<211> LENGTH: 76
<212> TYPE: DNA
<213> ORGANISM: Artificial Sequence
<220> FEATURE:
<223> OTHER INFORMATION: fragment

<400> SEQUENCE: 22
ctagtgacaa aactcacacc tgcccgccgt gcccggcgac ctgcccgccg tgcccggcgt      60
gatgaggatc caagct                                                     76

<210> SEQ ID NO 23
<211> LENGTH: 76
<212> TYPE: DNA
<213> ORGANISM: Artificial Sequence
<220> FEATURE:
<223> OTHER INFORMATION: fragment

<400> SEQUENCE: 23
ctagtgacaa aactcacaca tgcccgccgt gcccggcgac ctgcccgccg tgcccggcgt      60
gatgaggatc caagct                                                     76

<210> SEQ ID NO 24
<211> LENGTH: 20
<212> TYPE: PRT
<213> ORGANISM: Artificial Sequence
<220> FEATURE:
<223> OTHER INFORMATION: fragment

<400> SEQUENCE: 24

Thr Ser Asp Lys Thr His Thr Cys Pro Pro Cys Pro Ala Thr Cys Pro
  1               5                  10                  15

Pro Cys Pro Ala
            20

<210> SEQ ID NO 25
<211> LENGTH: 78
<212> TYPE: DNA
<213> ORGANISM: Artificial Sequence
<220> FEATURE:
<223> OTHER INFORMATION: fragment

<400> SEQUENCE: 25
ctagtgacaa aactcacacc tgcccgccgt gcccggcggg aacctgcccg ccgtgcccgg      60
cgtgatgagg atccaagc                                                   78

<210> SEQ ID NO 26
<211> LENGTH: 21
<212> TYPE: PRT
<213> ORGANISM: Artificial Sequence
<220> FEATURE:
<223> OTHER INFORMATION: fragment

<400> SEQUENCE: 26

Thr Ser Asp Lys Thr His Thr Cys Pro Pro Cys Pro Ala Gly Thr Cys
  1               5                  10                  15

Pro Pro Cys Pro Ala
            20

<210> SEQ ID NO 27
<211> LENGTH: 82
<212> TYPE: DNA
<213> ORGANISM: Artificial Sequence
```

```
<220> FEATURE:
<223> OTHER INFORMATION: fragment

<400> SEQUENCE: 27
ctagtgacaa aactcacacc tgcccgccgt gcccggcggg aggaacctgc cgccgtgcc      60 cggcgtgatg aggatccaag ct                                             82

<210> SEQ ID NO 28
<211> LENGTH: 22
<212> TYPE: PRT
<213> ORGANISM: Artificial Sequence
<220> FEATURE:
<223> OTHER INFORMATION: fragment

<400> SEQUENCE: 28

Thr Ser Asp Lys Thr His Thr Cys Pro Pro Cys Pro Ala Gly Gly Thr
 1               5                  10                  15

Cys Pro Pro Cys Pro Ala
            20

<210> SEQ ID NO 29
<211> LENGTH: 84
<212> TYPE: DNA
<213> ORGANISM: Artificial Sequence
<220> FEATURE:
<223> OTHER INFORMATION: fragment

<400> SEQUENCE: 29
ctagtgacaa aactcacacc tgcccgccgt gcccggcggg aggaggaacc tgcccgccgt    60
gcccggcgtg atgaggatcc aagc                                           84

<210> SEQ ID NO 30
<211> LENGTH: 23
<212> TYPE: PRT
<213> ORGANISM: Artificial Sequence
<220> FEATURE:
<223> OTHER INFORMATION: fragment

<400> SEQUENCE: 30

Thr Ser Asp Lys Thr His Thr Cys Pro Pro Cys Pro Ala Gly Gly Gly
 1               5                  10                  15

Thr Cys Pro Pro Cys Pro Ala
            20

<210> SEQ ID NO 31
<211> LENGTH: 88
<212> TYPE: DNA
<213> ORGANISM: Artificial Sequence
<220> FEATURE:
<223> OTHER INFORMATION: fragment

<400> SEQUENCE: 31
ctagtgacaa aactcacacc tgcccgccgt gcccggcggg aggaggagga acctgcccgt    60 gctgccggc gtgatgagga tccaagct                                        88

<210> SEQ ID NO 32
<211> LENGTH: 50
<212> TYPE: DNA
<213> ORGANISM: Artificial Sequence
<220> FEATURE:
<223> OTHER INFORMATION: fragment

<400> SEQUENCE: 32
```
thrsrasyst hrhsthrcys rrcysraagy gygygythrc ysrrcysraa          50

<210> SEQ ID NO 33
<211> LENGTH: 91
<212> TYPE: DNA
<213> ORGANISM: Artificial Sequence
<220> FEATURE:
<223> OTHER INFORMATION: fragment

<400> SEQUENCE: 33
ctagtgacaa aactcacacc tgcccgccgt gcccggcgaa aggcaaaggc gaaacctgcc     60
cgtgctgccc ggcgtgatga ggatccaagc t                                   91

<210> SEQ ID NO 34
<211> LENGTH: 25
<212> TYPE: PRT
<213> ORGANISM: Artificial Sequence
<220> FEATURE:
<223> OTHER INFORMATION: fragment

<400> SEQUENCE: 34

Thr Ser Asp Lys Thr His Thr Cys Pro Pro Cys Pro Ala Lys Gly Lys
  1               5                  10                  15

Gly Glu Thr Cys Pro Pro Cys Pro Ala
             20                  25

<210> SEQ ID NO 35
<211> LENGTH: 73
<212> TYPE: DNA
<213> ORGANISM: Artificial Sequence
<220> FEATURE:
<223> OTHER INFORMATION: fragment

<400> SEQUENCE: 35
ctagtgacaa aactcacaca tgcccgccgt gcccgacctg cccgccgtgc ccggcgtgat     60
gaggatccaa gct                                                       73

<210> SEQ ID NO 36
<211> LENGTH: 19
<212> TYPE: PRT
<213> ORGANISM: Artificial Sequence
<220> FEATURE:
<223> OTHER INFORMATION: fragment

<400> SEQUENCE: 36

Thr Ser Asp Lys Thr His Thr Cys Pro Pro Cys Pro Thr Cys Pro Pro
  1               5                  10                  15

Cys Pro Ala

<210> SEQ ID NO 37
<211> LENGTH: 70
<212> TYPE: DNA
<213> ORGANISM: Artificial Sequence
<220> FEATURE:
<223> OTHER INFORMATION: fragment

<400> SEQUENCE: 37
ctagtgacaa aactcacaca tgcccgccgt gcccgtgccc gccgtgcccg gcgtgatgag     60
gatccaagct                                                           70

<210> SEQ ID NO 38
<211> LENGTH: 18
<212> TYPE: PRT

<213> ORGANISM: Artificial Sequence
<220> FEATURE:
<223> OTHER INFORMATION: fragment

<400> SEQUENCE: 38

Thr Ser Asp Lys Thr His Thr Cys Pro Pro Cys Pro Cys Pro Pro Cys
1               5                   10                  15

Pro Ala

<210> SEQ ID NO 39
<211> LENGTH: 104
<212> TYPE: DNA
<213> ORGANISM: Artificial Sequence
<220> FEATURE:
<223> OTHER INFORMATION: fragment

<400> SEQUENCE: 39
ctagtgacaa aactcacacc tgcccgccgt gcccggcgac ctgcccgccg tgcccggcga    60
cctgcccgcc gtgcccggcg tgatgaggat ccaagcttgc ggcc                   104

<210> SEQ ID NO 40
<211> LENGTH: 27
<212> TYPE: PRT
<213> ORGANISM: Artificial Sequence
<220> FEATURE:
<223> OTHER INFORMATION: fragment

<400> SEQUENCE: 40

Thr Ser Asp Lys Thr His Thr Cys Pro Pro Cys Pro Ala Thr Cys Pro
1               5                   10                  15

Pro Cys Pro Ala Thr Cys Pro Pro Cys Pro Ala
            20                  25

<210> SEQ ID NO 41
<211> LENGTH: 122
<212> TYPE: DNA
<213> ORGANISM: Artificial Sequence
<220> FEATURE:
<223> OTHER INFORMATION: fragment

<400> SEQUENCE: 41
ctagtgacaa aactcacacc tgcccgccgt gcccggcggg caaaccgacc ctgtataacg    60
tgagcctggt gatgagcgat accgcgggca cctgttattg atgaggatcc aagcttgcgg   120
cc                                                                 122

<210> SEQ ID NO 42
<211> LENGTH: 33
<212> TYPE: PRT
<213> ORGANISM: Artificial Sequence
<220> FEATURE:
<223> OTHER INFORMATION: fragment

<400> SEQUENCE: 42

Thr Ser Asp Lys Thr His Thr Cys Pro Pro Cys Pro Ala Gly Lys Pro
1               5                   10                  15

Thr Leu Tyr Asn Val Ser Leu Val Met Ser Asp Thr Ala Gly Thr Cys
                20                  25                  30

Tyr

<210> SEQ ID NO 43
<211> LENGTH: 122
<212> TYPE: DNA
<213> ORGANISM: Artificial Sequence
<220> FEATURE:
<223> OTHER INFORMATION: fragment

<400> SEQUENCE: 43

```
ctagtgacaa aactcacacc tgcccgccgt gcccggcggg caaaccgacc catgtgaacg      60
tgagcgtggt gatggcggaa gtggatggca cctgttattg atgaggatcc aagcttgcgg     120
cc                                                                   122
```

<210> SEQ ID NO 44
<211> LENGTH: 33
<212> TYPE: PRT
<213> ORGANISM: Artificial Sequence
<220> FEATURE:
<223> OTHER INFORMATION: fragment

<400> SEQUENCE: 44

Thr Ser Asp Lys Thr His Thr Cys Pro Pro Cys Pro Ala Gly Lys Pro
1               5                   10                  15

Thr His Val Asn Val Ser Val Val Met Ala Glu Val Asp Gly Thr Cys
            20                  25                  30

Tyr

<210> SEQ ID NO 45
<211> LENGTH: 74
<212> TYPE: DNA
<213> ORGANISM: Artificial Sequence
<220> FEATURE:
<223> OTHER INFORMATION: fragment

<400> SEQUENCE: 45

```
ctagtgacaa aactcacacc tgctgcgtgg aatgcccgcc gtgcccggcg tgatgaggat      60
ccaagcttgc ggcc                                                       74
```

<210> SEQ ID NO 46
<211> LENGTH: 17
<212> TYPE: PRT
<213> ORGANISM: Artificial Sequence
<220> FEATURE:
<223> OTHER INFORMATION: fragment

<400> SEQUENCE: 46

Thr Ser Asp Lys Thr His Thr Cys Cys Val Glu Cys Pro Pro Cys Pro
1               5                   10                  15

Ala

<210> SEQ ID NO 47
<211> LENGTH: 107
<212> TYPE: DNA
<213> ORGANISM: Artificial Sequence
<220> FEATURE:
<223> OTHER INFORMATION: fragment

<400> SEQUENCE: 47

```
ctagtgacaa aactcacacc tgcccgcgtt gccggaacc gaaaagctgc gatacccgc       60 cgccgtgccc gcgttgcccg gcgtgatgag gatccaagct tgcggcc                  107
```

<210> SEQ ID NO 48
<211> LENGTH: 28
<212> TYPE: PRT
<213> ORGANISM: Artificial Sequence
<220> FEATURE:
<223> OTHER INFORMATION: fragment

```
<400> SEQUENCE: 48

Thr Ser Asp Lys Thr His Thr Cys Pro Arg Cys Pro Glu Pro Lys Ser
1               5                   10                  15

Cys Asp Thr Pro Pro Cys Pro Arg Cys Pro Ala
            20                  25

<210> SEQ ID NO 49
<211> LENGTH: 62
<212> TYPE: DNA
<213> ORGANISM: Artificial Sequence
<220> FEATURE:
<223> OTHER INFORMATION: fragment

<400> SEQUENCE: 49
ctagtgacaa aactcacacc tgcccgagct gcccggcgtg atgaggatcc aagcttgcgg    60
cc                                                                  62

<210> SEQ ID NO 50
<211> LENGTH: 13
<212> TYPE: PRT
<213> ORGANISM: Artificial Sequence
<220> FEATURE:
<223> OTHER INFORMATION: fragment

<400> SEQUENCE: 50

Thr Ser Asp Lys Thr His Thr Cys Pro Ser Cys Pro Ala
1               5                   10

<210> SEQ ID NO 51
<211> LENGTH: 52
<212> TYPE: DNA
<213> ORGANISM: Artificial Sequence
<220> FEATURE:
<223> OTHER INFORMATION: fragment

<400> SEQUENCE: 51
acttgtgaca aaactcacac atgcccgccg tgcccggcgt gatgaggatc ca            52

<210> SEQ ID NO 52
<211> LENGTH: 13
<212> TYPE: PRT
<213> ORGANISM: Artificial Sequence
<220> FEATURE:
<223> OTHER INFORMATION: fragment

<400> SEQUENCE: 52

Thr Cys Asp Lys Thr His Thr Cys Pro Pro Cys Pro Ala
1               5                   10

<210> SEQ ID NO 53
<211> LENGTH: 73
<212> TYPE: DNA
<213> ORGANISM: Artificial Sequence
<220> FEATURE:
<223> OTHER INFORMATION: fragment

<400> SEQUENCE: 53
acttgtgaca aaactcacac atgcccgccg tgcccggcga cctgcccgcc gtgcccggcg    60
tgatgaggat cca                                                      73

<210> SEQ ID NO 54
<211> LENGTH: 20
<212> TYPE: PRT
```

```
<213> ORGANISM: Artificial Sequence
<220> FEATURE:
<223> OTHER INFORMATION: fragment

<400> SEQUENCE: 54

Thr Cys Asp Lys Thr His Thr Cys Pro Pro Cys Pro Ala Thr Cys Pro
1               5                   10                  15

Pro Cys Pro Ala
            20

<210> SEQ ID NO 55
<211> LENGTH: 20
<212> TYPE: PRT
<213> ORGANISM: Artificial Sequence
<220> FEATURE:
<223> OTHER INFORMATION: fragment

<400> SEQUENCE: 55

Thr Ser Asp Lys Thr His Thr Cys Pro Pro Cys Pro Ala Thr Cys Pro
1               5                   10                  15

Pro Cys Pro Ala
            20
```